(12) United States Patent
Honjo et al.

(10) Patent No.: US 11,071,524 B2
(45) Date of Patent: Jul. 27, 2021

(54) ANALYZING APPARATUS

(71) Applicant: CANON MEDICAL SYSTEMS CORPORATION, Otawara (JP)

(72) Inventors: Yasunori Honjo, Kawasaki (JP); Masaki Watanabe, Kawasaki (JP); Tetsuya Kawagishi, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1105 days.

(21) Appl. No.: 15/367,712

(22) Filed: Dec. 2, 2016

(65) Prior Publication Data
US 2017/0156700 A1 Jun. 8, 2017

(30) Foreign Application Priority Data

Dec. 4, 2015 (JP) .............................. JP2015-237845
Nov. 24, 2016 (JP) .............................. JP2016-228341

(51) Int. Cl.
A61B 8/00 (2006.01)
A61B 8/08 (2006.01)
G01S 7/52 (2006.01)

(52) U.S. Cl.
CPC ............. A61B 8/485 (2013.01); A61B 8/08 (2013.01); A61B 8/5223 (2013.01); G01S 7/52042 (2013.01); G01S 7/52074 (2013.01)

(58) Field of Classification Search
None
See application file for complete search history.

(56) References Cited

U.S. PATENT DOCUMENTS

| 9,125,547 | B2 | 9/2015 | Xie et al. | |
|---|---|---|---|---|
| 2013/0109982 | A1* | 5/2013 | Sato | A61B 5/02014 600/502 |
| 2013/0133783 | A1 | 5/2013 | Yamaguchi et al. | |
| 2014/0018679 | A1 | 1/2014 | Chen et al. | |
| 2015/0133783 | A1 | 5/2015 | Tabaru et al. | |
| 2015/0164480 | A1* | 6/2015 | Watanabe | A61B 8/463 600/438 |
| 2015/0173718 | A1 | 6/2015 | Tabaru et al. | |
| 2015/0335313 | A1* | 11/2015 | Xie | A61B 8/00 600/438 |

FOREIGN PATENT DOCUMENTS

| CN | 101869485 A | 10/2010 |
|---|---|---|
| CN | 104302233 A | 1/2015 |

(Continued)

OTHER PUBLICATIONS

Combined Chinese Office Action and Search Report dated Jun. 5, 2019 Chinese Patent Application No. 201611093028.X, 13 pages.

(Continued)

Primary Examiner — Joel F Brutus
(74) Attorney, Agent, or Firm — Oblon, McClelland, Maier & Neustadt, L.L.P.

(57) ABSTRACT

An analyzing apparatus according to an embodiment includes processing circuitry. The processing circuitry is configured to detect a shear wave propagating in an object. The processing circuitry is configured to calculate an index value that indicates viscosity within the object and that is not dependent on any physical model related to viscoelasticity, by analyzing the detected shear wave.

20 Claims, 14 Drawing Sheets

(56) References Cited

FOREIGN PATENT DOCUMENTS

| | | |
|---|---|---|
| CN | 104622502 A | 5/2015 |
| JP | 2008-161674 | 7/2008 |
| JP | 2013-141575 | 7/2013 |
| JP | 2015-92937 | 5/2015 |
| JP | 2015-131097 A1 | 7/2015 |
| WO | WO 2012/063928 A1 | 5/2012 |
| WO | WO 2014/136502 A1 | 9/2014 |
| WO | WO 2014/20102 A1 | 12/2014 |

OTHER PUBLICATIONS

Shigao Chen, et al. "Shearwave Dispersion Ultrasound Vibrometry (SDUV) for Measuring Tissue Elasticity and Viscosity", IEEE Transactions on Ultrasonics, Ferroelectrics, and Frequency Control, vol. 56, No. 1, 2009, 8 pages.

Chinese Office Action dated Aug. 10, 2020, in Patent Application No. 201611093028.X, 6 pages.

Japanese Office Action dated Sep. 8, 2020 in Patent Application No. 2016-228341, 5 pages.

Alireza Nabavizadehrafsanjani, et al., "Model-Free Compression Creep Methods for Differentiation of Lesion from Background Tissue" IEEE International Ultrasonics Symposium Proceedings, vol. 4, 2012, pp. 2533-2535.

Ivan Z. Nenadic, et al., "Application of Attenuation Measuring Ultrasound Shearwave Elastagraphy in 8 Post-Transplant Liver Patients" IEEE International Ultrasonics Symposium Proceedings. vol. 2, 2014. pp. 987-990.

Japanese Office Action dated Feb. 24, 2021, issued in Japanese Patent Application No. 2016-228341.

Chinese Office Action dated Feb. 7, 2021, issued in Chinese Patent Application No. 201611093028.X.

* cited by examiner

FIG.9
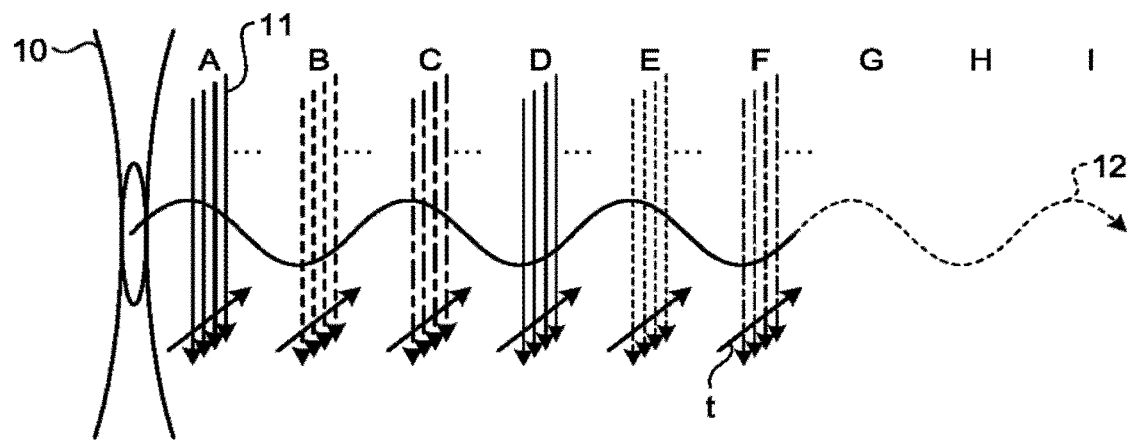
FIG.10
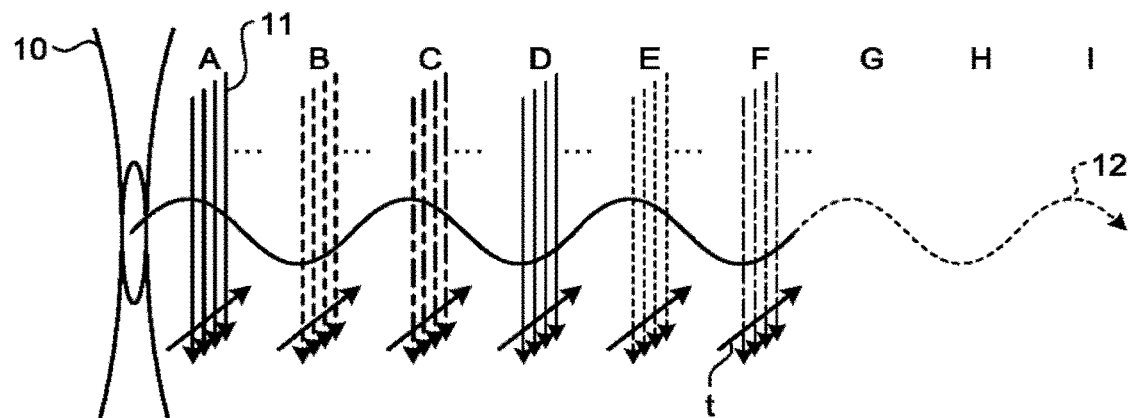
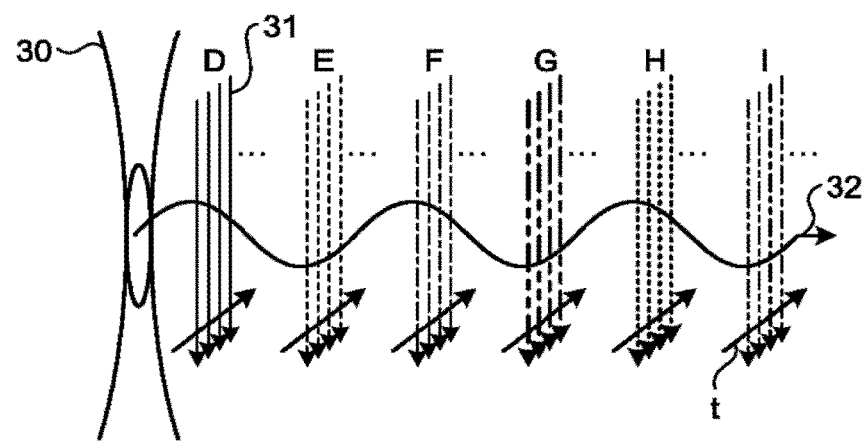

ANALYZING APPARATUS

CROSS-REFERENCE TO RELATED APPLICATIONS

This application is based upon and claims the benefit of priority from Japanese Patent Application No. 2015-237845, filed on Dec. 4, 2015; and Japanese Patent Application No. 2016-228341, filed on Nov. 24, 2016, the entire contents of all of which are incorporated herein by reference.

FIELD

The embodiments described herein relate generally to an analyzing apparatus.

BACKGROUND

Tissues in patients' bodies are considered as viscoelastic members having viscosity and elasticity. In recent years, to evaluate viscoelasticity, various methods have been proposed. For example, elastography is known as a method by which levels of firmness (elasticity) of a tissue in a human body (patient's body) are measured so as to express a distribution of the measured firmness levels in a picture. For example, examples of known processes include a Shear Wave Elastography (SWE) process by which displacements based on a shear wave are caused by applying an acoustic radiation force to a tissue in a human body, so that propagation velocity of the shear wave is calculated by chronologically measuring the displacements that were caused, and a modulus of elasticity is calculated from the calculated propagation velocity.

Further, for example, to evaluate viscoelasticity, a method has been used by which a value serving as an index of viscosity is calculated by approximating a human body to a model. In this situation, the model denotes, for example, an approximate expression that expresses phenomena related to viscosity and elasticity in a mathematical formula, and known examples include a Maxwell model, a Voigt model, a three-element model, and a multi-dimensional Maxwell model. However, it is reported that values indicating viscoelasticity may vary due to differences among models used for the evaluation.

BRIEF DESCRIPTION OF THE DRAWINGS

FIG. 9 is a drawing for explaining attenuation of a shear wave;

FIG. 10 is a drawing for explaining a process performed by a processing circuit according to a second embodiment;

DETAILED DESCRIPTION

An analyzing apparatus according to an embodiment includes processing circuitry. The processing circuitry is configured to detect a shear wave propagating in an object. The processing circuitry is configured to calculate an index value that indicates viscosity within the object and that is not dependent on any physical model related to viscoelasticity, by analyzing the detected shear wave.

Exemplary embodiments of an analyzing apparatus will be explained below, with reference to the accompanying drawings. In the following sections, an ultrasound diagnosis apparatus will be explained as an example of the analyzing apparatus.

First Embodiment

Figure 1:
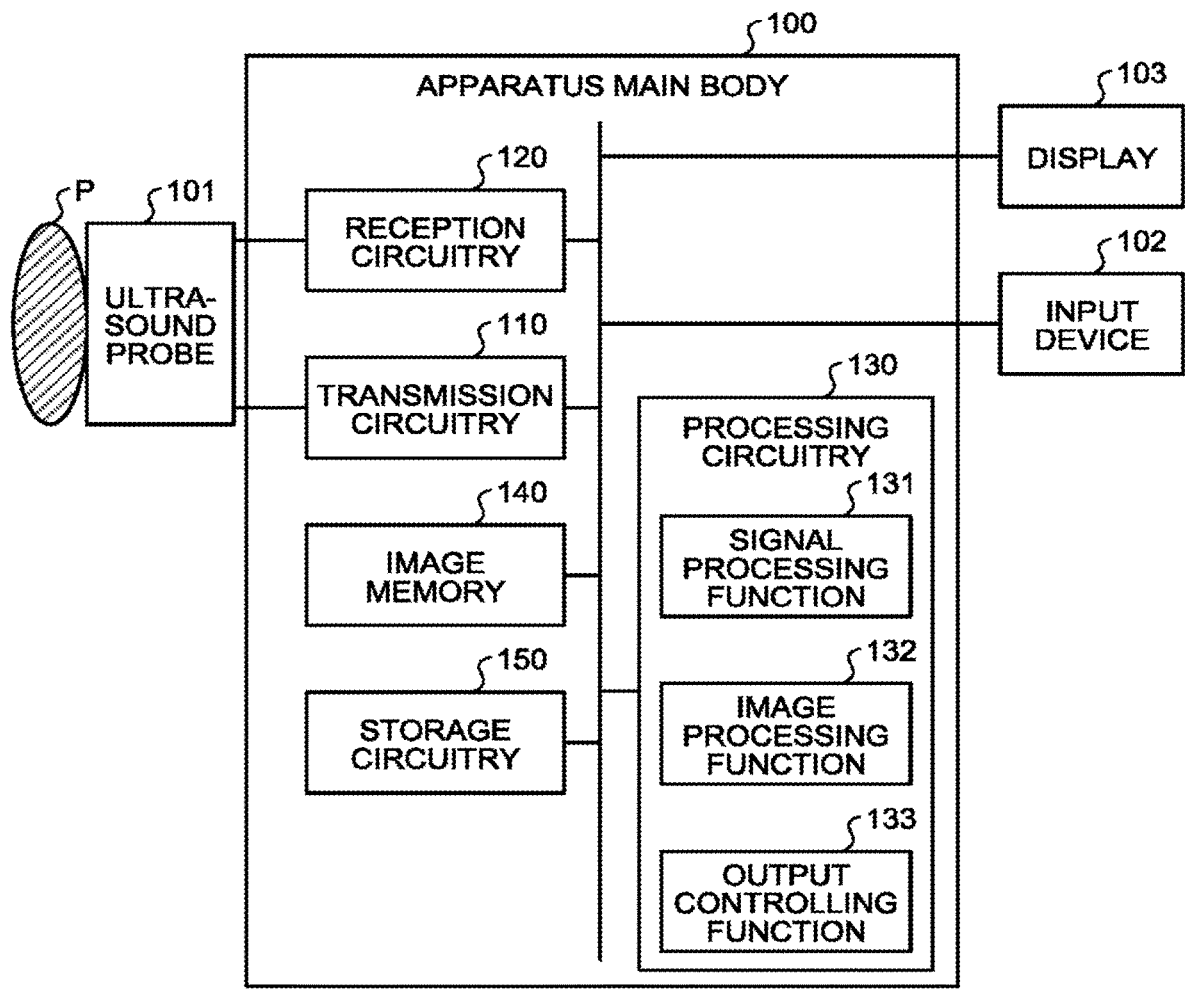
FIG. 1 is a block diagram illustrating an exemplary configuration of an ultrasound diagnosis apparatus according to a first embodiment.

FIG. 1 is a block diagram illustrating an exemplary configuration of an ultrasound diagnosis apparatus according to a first embodiment. As illustrated in FIG. 1, the ultrasound diagnosis apparatus according to the first embodiment includes an ultrasound probe 101, an input device 102, a display 103, and an apparatus main body 100. The ultrasound probe 101, the input device 102, and the display 103 are connected to the apparatus main body 100 so as to be able to communicate therewith. An examined subject (hereinafter "patient") P is not included in the configuration of the ultrasound diagnosis apparatus.

The ultrasound probe 101 includes a plurality of transducer elements (e.g., piezoelectric transducer elements), which are configured to generate an ultrasound wave on the basis of a drive signal supplied thereto from transmission circuitry 110 (explained later) included in the apparatus main body 100. Further, the plurality of transducer elements included in the ultrasound probe 101 are configured to receive a reflected wave from the patient P and to convert the received reflected wave into an electric signal. Further, the ultrasound probe 101 includes matching layers provided for the transducer elements, as well as a backing member or the like that prevents ultrasound waves from propagating rearward from the transducer elements. The ultrasound probe 101 is detachably connected to the apparatus main body 100.

When an ultrasound wave is transmitted from the ultrasound probe 101 to the patient P, the transmitted ultrasound wave is repeatedly reflected on a surface of discontinuity of acoustic impedances at a tissue in the body of the patient P and is received as a reflected-wave signal by the plurality of transducer elements included in the ultrasound probe 101. The amplitude of the received reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction.

The first embodiment is applicable to any of the situations where the ultrasound probe 101 illustrated in FIG. 1 is: a one-dimensional ultrasound probe in which the plurality of piezoelectric transducer elements are arranged in a row; a one-dimensional ultrasound probe in which the plurality of piezoelectric transducer elements arranged in a row are mechanically swayed; or a two-dimensional ultrasound probe in which the plurality of piezoelectric transducer elements are two-dimensionally arranged in a grid formation.

The input device 102 includes a mouse, a keyboard, a button, a panel switch, a touch command screen, a foot switch, a trackball, and/or a joystick. The input device 102 is configured to receive various types of setting requests from an operator of the ultrasound diagnosis apparatus and to transfer the received various types of setting requests to the apparatus main body 100.

The display 103 is configured to display a Graphical User Interface (GUI) used by the operator of the ultrasound diagnosis apparatus to input the various types of setting requests through the input device 102 and to display ultrasound image data generated by the apparatus main body 100 or the like.

The apparatus main body 100 is an apparatus configured to generate the ultrasound image data on the basis of the reflected-wave signal received by the ultrasound probe 101. As illustrated in FIG. 1, the apparatus main body 100 includes the transmission circuitry 110, reception circuitry 120, processing circuitry 130, an image memory 140, and storage circuitry 150. The transmission circuitry 110, the reception circuitry 120, the processing circuitry 130, the image memory 140, and the storage circuitry 150 are connected to one another so as to be able to communicate with one another.

The transmission circuitry 110 is configured to control transmission directionality in ultrasound transmissions. More specifically, the transmission circuitry 110 includes a rate pulser generator, a transmission delay unit, a transmission pulser, and the like and is configured to supply the drive signal to the ultrasound probe 101. The rate pulser generator is configured to repeatedly generate a rate pulse used for forming a transmission ultrasound wave, at a predetermined rate frequency called a Pulse Repetition Frequency (PRF). The rate pulse applies a voltage to the transmission pulser, while having mutually-different transmission delay periods as a result of going through the transmission delay unit. In other words, the transmission delay unit applies the transmission delay period that is required to converge the ultrasound wave generated by the ultrasound probe 101 into the form of a beam and to determine transmission directionality and that corresponds to each of the transducer elements, to each of the rate pulses generated by the rate pulser generator. Further, the transmission pulser applies the drive signal (a drive pulse) to the ultrasound probe 101 with timing based on the rate pulses. The transmission directions and the transmission delay periods are stored in the storage circuitry 150 (explained later), so that the transmission circuitry 110 controls the transmission directionality by referring to the storage circuitry 150.

The drive pulse is transferred from the transmission pulser to the transducer elements provided in the ultrasound probe 101 via a cable and is subsequently converted from the electric signal into mechanical vibration by the transducer elements. The mechanical vibration is transmitted within the body of the patient as the ultrasound wave. The ultrasound wave has the mutually-different transmission delay periods corresponding to the transducer elements and is converged and propagates in predetermined directions. By varying the transmission delay periods applied to the rate pulses, the transmission delay unit is able to arbitrarily adjust the transmission directions from the transducer element surfaces. The transmission circuitry 110 gives the transmission directionality by controlling the quantity and the positions (transmission openings) of the transducer elements used for transmitting the ultrasound beam as well as the transmission delay periods corresponding to the positions of the transducer elements forming the transmission openings. For example, the transmission delay circuit included in the transmission circuitry 110 controls the position of a convergence point (a transmission focus) in the depth direction of an ultrasound transmission, by applying the transmission delay periods to the rate pulses generated by the pulse circuit.

In this situation, the transmission circuitry 110 has a function to be able to instantly change the transmission frequency, the transmission drive voltage, and the like, for the purpose of executing a predetermined scanning sequence on the basis of an instruction from the processing circuitry 130 (explained later). In particular, the configuration to change the transmission drive voltage is realized by using a linear-amplifier-type transmission circuit of which the value can be instantly switched or by using a mechanism configured to electrically switch between a plurality of power source units.

The reflected wave of the ultrasound wave transmitted by the ultrasound probe 101 reaches the transducer elements provided in the ultrasound probe 101 and is converted from the mechanical vibration into the electric signal (the reflected-wave signal) by the transducer elements, before being input to the reception circuitry 120.

The reception circuitry 120 is configured to control reception directionality during ultrasound receptions. More specifically, the reception circuitry 120 includes a pre-amplifier, an Analog/Digital (A/D) converting unit, a reception delay unit, an adding unit, and the like. The reception circuitry 120 is configured to generate reflected-wave data by performing various types of processes on the reflected-wave signal received by the ultrasound probe 101. The pre-amplifier performs a gain correcting process by amplifying the reflected-wave signal for each of the channels. The A/D converting unit is configured to apply an A/D conversion to the gain-corrected reflected-wave signals. The reception delay unit is configured to apply a reception delay period required to determine the reception directionality for each of the channels. The adding unit is configured to generate the reflected-wave data by performing an adding process on the reflected-wave signals (digital signals) to which the reception delay period has been applied. As a result of the adding process performed by the adding unit, reflected components from the direction corresponding to the reception directionality of the reflected-wave signals are emphasized. The reception directions and the reception delay periods are stored in the storage circuitry 150 (explained later), so that the reception circuitry 120 controls the reception directionality by referring to the storage circuitry 150. Further, the reception circuitry 120 according to the first embodiment is also capable of performing parallel simultaneous reception.

The processing circuitry 130 is configured to control the entire processes performed by the ultrasound diagnosis apparatus. More specifically, the processing circuitry 130 is configured to control processes performed by the transmission circuitry 110 and the reception circuitry 120 on the basis of the various types of setting requests input thereto from the operator via the input device 102 and various types of control computer programs and various types of data read from the storage circuitry 150. The processing circuitry 130 is an example of a processing unit.

Further, the processing circuitry 130 executes a signal processing function 131, an image processing function 132, and an output controlling function 133. In this situation, the processing functions executed by the constituent elements of the processing circuitry 130 such as the signal processing function 131, the image processing function 132, and the output controlling function 133 are recorded in the storage circuitry 150 in the form of a computer-executable program. The processing circuitry 130 is a processor configured to realize the functions corresponding to the computer programs (hereinafter, "programs") by reading and executing the programs from the storage circuitry 150. In other words, the signal processing function 131 is a function realized as a result of the processing circuitry 130 reading and executing the program corresponding to the signal processing function 131 from the storage circuitry 150. Further, the image processing function 132 is a function realized as a result of the processing circuitry 130 reading and executing the program corresponding to the image processing function 132 from the storage circuitry 150. Also, the output controlling function 133 is a function realized as a result of the processing circuitry 130 reading and executing the program corresponding to the output controlling function 133 from the storage circuitry 150. In other words, the processing circuitry 130 that has read the programs has the functions illustrated within the processing circuitry 130 in FIG. 1.

The signal processing function 131 is configured to perform various types of signal processing processes on the reflected-wave data generated by the reception circuitry 120 from the reflected-wave signals. The signal processing function 131 is configured to generate data (B-mode data) in which the signal intensity at each sampling point is expressed as a level of brightness, by performing a logarithmic amplifying process, an envelope detecting process, or the like on the reflected-wave data received from the reception circuitry 120.

Further, by using the reflected-wave data received from the reception circuitry 120, the signal processing function 131 generates data (Doppler data) obtained by extracting motion information based on the Doppler effect exerted on moving members at each of the sampling points within a scanned region. More specifically, the signal processing function 131 generates the Doppler data obtained by extracting, as the motion information of the moving members, an average velocity value, a variance value, a power value, and the like at each of the sampling points. In this situation, the moving members may be, for example, blood flows, tissues such as cardiac walls, a contrast agent, and the like.

The image processing function 132 is configured to generate ultrasound image data from the data generated by the signal processing function 131. From the B-mode data generated by the signal processing function 131, the image processing function 132 generates B-mode image data in which the intensity of the reflected-wave is expressed as a level of brightness. Further, from the Doppler data generated by the signal processing function 131, the image processing function 132 generates Doppler image data expressing moving member information. The Doppler image data may be velocity image data, variance image data, power image data, or image data combining any of these types of data together.

Generally speaking, the image processing function 132 is configured to convert (by performing a scan convert process) a scanning line signal sequence from an ultrasound scan into a scanning line signal sequence in a video format used by, for example, television and to generate ultrasound image data for a display purpose. More specifically, the image processing function 132 generates the display-purpose ultrasound image data by performing a coordinate converting process in accordance with the ultrasound scanning mode used by the ultrasound probe 101. Further, as various types of image processing processes other than the scan convert process, the image processing function 132 performs, for example, an image processing process (a smoothing process) to re-generate a brightness average value image by using a plurality of image frames resulting from the scan convert process, an image processing process (an edge emphasizing process) using a differential filter within an image, or the like. Further, the image processing function 132 combines additional information (text information of various types of parameters, scale graduations, body marks, and/or the like) with the ultrasound image data.

In other words, the B-mode data, the Doppler data, and firmness distribution information are each ultrasound image data before the scan convert process is performed. In contrast, the data generated by the image processing function 132 is the display-purpose ultrasound image data after the scan convert process is performed. When the signal processing function 131 has generated three-dimensional data (three-dimensional B-mode data, three-dimensional Doppler data, and three-dimensional firmness distribution information), the image processing function 132 generates volume data by performing a coordinate converting process in accordance with the ultrasound scanning mode used by the ultrasound probe 101. After that, the image processing function 132 generates display-purpose two-dimensional image data by performing various types of rendering processes on the volume data.

The output controlling function 133 is configured to exercise output control over the information generated by the processing circuitry 130. For example, the output controlling function 133 exercises control so that the display-purpose ultrasound image data stored in the image memory 140 is displayed on the display 103. Further, for example, the output controlling function 133 transmits the ultrasound image data to an apparatus such as a workstation, in response to an instruction from the operator.

The image memory 140 is a memory configured to store therein the display-purpose image data generated by the image processing function 132. Further, the image memory 140 is also capable of storing therein the data generated by the signal processing function 131. The B-mode data, the Doppler data, and the firmness distribution information stored in the image memory 140 may be, for example, invoked by the operator after a diagnosis procedure and serve as display-purpose ultrasound image data after being routed through the image processing function 132.

The storage circuitry 150 is configured to store therein a control computer program used for performing ultrasound transmissions/receptions, image processing processes, and displaying processes, as well as various types of data such as diagnosis information (e.g., patients' IDs, observations of medical doctors, etc.), diagnosis protocols, various types of body marks, and the like. Further, the storage circuitry 150 may also be used for storing therein any of the image data stored in the image memory 140, as necessary. Further, it is also possible to transfer any of the data stored in the storage circuitry 150 to an external apparatus via an interface unit (not illustrated).

Further, in the first embodiment, the example is explained in which the single processing circuit (the processing circuitry 130) realizes the processing functions described above; however, a processing circuit may be structured by combining a plurality of independent processors together, so that the functions are realized as a result of the processors executing the programs. For example, besides the processing circuitry 130, the apparatus main body 100 may include a processor configured to execute the signal processing function 131 and a processor configured to execute the image processing function 132.

The term "processor" used in the above explanation denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processor realizes the functions by reading and executing the programs stored in the storage circuitry 150. It is also acceptable to directly incorporate the programs into the circuit of the processor, instead of storing the programs in the storage circuitry 150. In that situation, the processor realizes the functions by reading and executing the programs incorporated in the circuit thereof. Further, as for the processors according to the first embodiment, each of the processors may be structured as a single circuit. Alternatively, it is also acceptable to realize the functions thereof by structuring a single processor by combining together a plurality of independent circuits. Further, it is also acceptable to integrate the plurality of constituent elements illustrated in each of the drawings into one processor so as to realize the functions thereof.

In conventional ultrasound diagnosis apparatuses, as a method for evaluating viscoelasticity of a tissue in a human body, elastography is used by which a distribution of levels of firmness (elasticity) of the tissue in the human body is expressed in a picture. For example, examples of known processes include a Shear Wave Elastography (SWE) process by which displacements based on a shear wave are caused by applying an acoustic radiation force (a push pulse) to a tissue in a human body, so that propagation velocity of the shear wave is calculated by chronologically measuring the displacements that were caused, and a modulus of elasticity is calculated from the calculated propagation velocity. A firmness value measured by performing the SWE process is used as a quantitative index of elasticity in medical image diagnosis procedures, for example.

In this regard, tissues in patients' bodies are considered as viscoelastic members having viscosity and elasticity. For this reason, it is considered that it is possible to accurately understand viscoelastic characteristics of tissues in patients' bodies, by evaluating the viscosity, in addition to the evaluation of the elasticity through the SWE process.

However, among conventional viscosity evaluation methods, a commonly-used method is to approximate the human body to a model. Index values of viscosity calculated by using models have dependency on the models. For example, even when it is possible to perform an excellent measuring process on a phantom, it does not necessarily mean that it is possible to perform an excellent measuring process on a human body. Conversely, a model that is able to perform an excellent measuring process on a human body is not necessarily able to perform an excellent measuring process on a phantom.

To cope with this situation, the ultrasound diagnosis apparatus according to the first embodiment is configured to execute the functions described below, to evaluate the viscosity of a tissue in a human body. For example, the ultrasound diagnosis apparatus is configured to calculate an index value that is not dependent on any physical model related to viscoelasticity, by using frequency dependency of the velocity of a shear wave propagating through a viscous member.

For example, the ultrasound diagnosis apparatus according to the first embodiment is configured to calculate an index value related to frequency dependency of transverse wave velocity of a tissue in a human body, by causing the ultrasound probe 101 to transmit a push pulse to the tissue in the human body and further measuring a displacement by using a shear wave generated by the push pulse.

For example, the transmission circuitry 110 according to the first embodiment causes the ultrasound probe 101 to transmit, to the patient P, a push pulse (a displacement causing ultrasound wave) that causes a displacement by using a shear wave generated by an acoustic radiation force. Further, the transmission circuitry 110 according to the first embodiment causes the ultrasound probe 101 to transmit a tracking pulse (a measuring purpose ultrasound wave) multiple times for each of a plurality of scanning lines within a scanned region, the tracking pulse being used for measuring the displacements caused by the push pulse. The tracking pulse is transmitted for the purpose of measuring the shear wave generated by the push pulse at the sampling points within the scanned region.

Figure 2:
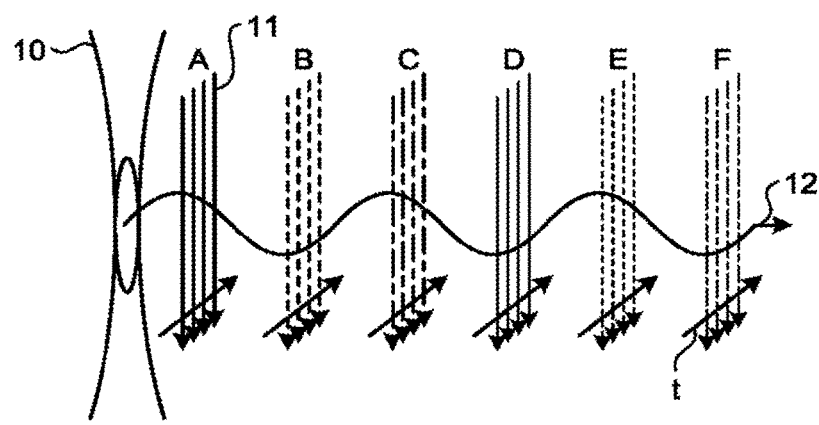
FIG. 2 is a drawing for explaining a process of measuring a shear wave performed by the ultrasound diagnosis apparatus according to the first embodiment.

FIG. 2 is a drawing for explaining the process of measuring the shear wave performed by the ultrasound diagnosis apparatus according to the first embodiment. FIG. 2 schematically illustrates a push pulse 10 and a tracking pulse 11 transmitted from the ultrasound probe 101. In FIG. 2, the arrow t corresponds to the time direction.

As illustrated in FIG. 2, when the push pulse 10 is transmitted, a displacement occurs from the transmission position of the push pulse 10. In this situation, for example, the displacement that occurred propagates as a shear wave 12 (a transverse wave) from the transmission position in the direction toward the right-hand side of the drawing and is transferred to the scanning lines A, B, C, D, E, and F, in the stated order. The shear wave 12 is measured by the tracking pulse 11 transmitted multiple times to each of the scanning lines (beams) A to F. In the example illustrated in FIG. 2, the tracking pulse 11 is transmitted four times to each of the scanning lines A to F. In FIG. 2 the tracking pulse 11 transmitted to each of the scanning lines A to F is illustrated by varying the type of the line.

The signal processing function 131 is configured to detect the shear wave 12 propagating in an object, in each of a plurality of positions arranged along the propagation direction of the shear wave 12. For example, by performing an auto-correlation calculation on the reflected-wave data of the tracking pulse 11 transmitted multiple times with respect to each of the scanning lines A to F, the signal processing function 131 estimates a displacement at each of the sampling points.

In this situation, there is a possibility that the estimated displacements include not only the displacements caused by the shear wave 12 but also displacements caused by respiration, pulsation, body movements, and the like. For this reason, by performing a filtering process using a Wall Filter (WF) or a direction filter, the signal processing function 131 estimates the displacement at each of the sampling points arranged along the propagation direction of the shear wave 12. In this manner, for example, the signal processing function 131 estimates the displacements caused by the shear wave, while excluding components of the displacements caused by respiration, pulsation, body movements, and the like from the estimated displacements. The WF is a filter configured to eliminate predetermined frequencies related to the respiration, the pulsation, the body movements, and the like. The direction filter is a filter configured to select displacements on an assumption that the shear wave 12 propagates in a horizontal direction.

In this manner, the signal processing function 131 detects a temporal change in the displacements at the sampling points, as the shear wave 12 propagating in the object. In this situation, due to the filter characteristics, because the filtering process using the WF or the direction filter may influence the phase characteristics calculated in a process performed thereafter, the filtering process does not necessarily have to be performed.

Figure 3:
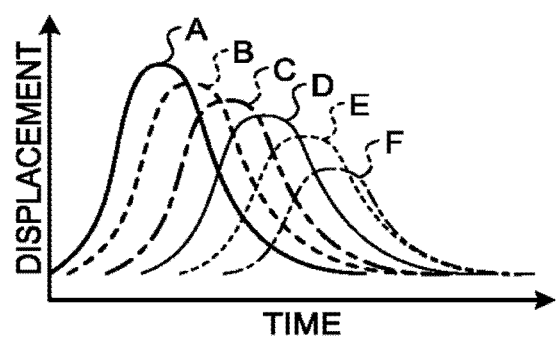
FIG. 3 is a drawing for explaining a process of detecting the shear wave performed by the ultrasound diagnosis apparatus according to the first embodiment.

FIG. 3 is a drawing for explaining the process of detecting the shear wave performed by the ultrasound diagnosis apparatus according to the first embodiment. FIG. 3 illustrates a chart (of time-displacement curves) indicating a temporal change in the displacement measured at each of the sampling points by the tracking pulse 11. The mutually-different types of lines in FIG. 3 correspond to the time-displacement curves at the sampling points on the scanning lines A to F.

As illustrated in FIG. 3, the signal processing function 131 estimates the displacements at different times, for each of the sampling points on the scanning lines A to F. In this situation, among the time-displacement curves detected at the different sampling points, the scanning line A positioned closest to the transmission position of the push pulse 10 exhibits the maximum displacement, and the curves become smaller as the distances from the transmission position to the scanning lines increase, in the order of the scanning lines B, C, D, E, F, and so on. In this manner, the signal processing function 131 detects the shear wave 12 propagating in the object, as the temporal change in the displacement at each of the sampling points.

The signal processing function 131 calculates the phase of each of a plurality of frequency components included in the detected shear wave 12. For example, the signal processing function 131 calculates the phase by performing a frequency analysis on the shear wave 12 detected in each of the plurality of positions. More specifically, by performing a Fourier transform on each of the obtained time-displacement curves in FIG. 3, the signal processing function 131 calculates the phase corresponding to each of the frequencies with respect to each of the sampling points.

Further, the time-displacement curves obtained at the sampling points are detected in the order along the propagation direction of the shear wave 12. For example, the peak positions of the time-displacement curves are detected at mutually-different times in the order along the propagation direction. Accordingly, the signal processing function 131 calculates time differences (disparities) among the time-displacement curves from the propagation time periods of the shear wave 12. For example, the propagation time periods may be calculated on the basis of a cross-correlation among the time-displacement curves at the sampling points or may be calculated by detecting the peaks of the time-displacement curves. Further, the signal processing function 131 performs a window function processing process after shifting an analysis range in accordance with the calculated time differences. In other words, before performing the frequency analysis, the signal processing function 131 performs the window function processing process by correcting the differences in the propagation time periods of the shear wave detected in the plurality of positions, with respect to the shear wave detected in each of the plurality of positions.

After that, by performing a Fourier transform on the time-displacement curves at the sampling points resulting from the window function processing process, the signal processing function 131 calculates the phase. In this situation, similarly to the WF or the direction filter, due to the filter characteristics of the window function, because the window function processing process may also influence the phase characteristics calculated in a process performed thereafter, the window function processing process does not necessarily have to be performed.

In the description above, the example is explained in which the Fourier transform is performed by using the displacements; however, possible embodiments are not limited to this example. For instance, the signal processing function 131 may detect the shear wave, by calculating movements within the object in a plurality of positions. For example, as the movements within the object, the signal processing function 131 may calculate displacements, velocity values, or acceleration values in a plurality of positions. In that situation, for example, the signal processing function 131 obtains information prior to an integral calculation as an instantaneous velocity value, by performing an auto-correlation calculation on the reflected-wave data. After that, the signal processing function 131 may evaluate frequency dependency by performing a Fourier transform on the obtained instantaneous velocity value.

By using the phases calculated with respect to the positions, the signal processing function 131 calculates a phase velocity value for each of the frequency components. For example, the signal processing function 131 calculates phase differences by using the phase calculated with respect to each of the sampling points. After that, by using Expression (1) presented below, the signal processing function 131 calculates a phase velocity value $C_{phase}$. In Expression (1), the symbols "$\Delta\phi$" denote a phase difference, whereas the character f denotes the frequency, and the character L denotes the distance between the sampling points.

$$C_{phase} = \frac{2\pi f \times L}{\Delta\phi} \quad (1)$$

For example, by using the phases calculated with respect to three or more positions, the signal processing function 131 calculates a phase velocity value. For example, by using the phases at three consecutive sampling points, the signal processing function 131 calculates a phase velocity value at the sampling point positioned in the middle among the three.

Figure 4:
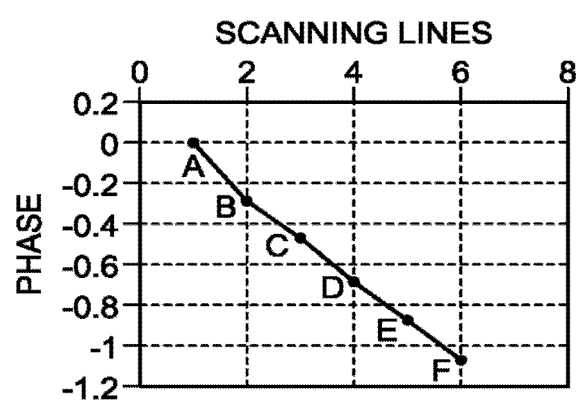
FIG. 4 is a drawing for explaining a process of calculating a phase velocity value performed by the ultrasound diagnosis apparatus according to the first embodiment.

FIG. 4 is a drawing for explaining the process of calculating the phase velocity values performed by the ultrasound diagnosis apparatus according to the first embodiment. FIG. 4 illustrates a chart plotting phases obtained with respect to a certain frequency in correspondence with the scanning lines A to F. In other words, in FIG. 4, the horizontal axis corresponds to the scanning lines, whereas the vertical axis corresponds to the phase.

As illustrated in FIG. 4, for example, the signal processing function 131 calculates the phase velocity value at a sampling point on the scanning line B, by using the phases at the sampling points on the scanning lines A, B, and C. In that situation, the phase difference Δφ in Expression (1) may be calculated from an average of the differences in the phase between the adjacently-positioned sampling points among the scanning lines A, B, and C or may be calculated from a slope by implementing a least-squares method on the phases at the sampling points on the scanning lines A, B, and C. Further, the distance L is calculated from the distance between a sampling point on the scanning line A and a sampling point on the scanning line C. Further, as the frequency f, a plurality of arbitrary frequencies are selected. For example, as the frequency f, a frequency at which the shear wave 12 is more dominant than respiration, pulsation, body movements, and the like are selected. After that, by using the phase difference Δφ, the distance L, and the frequency f that were calculated, the signal processing function 131 calculates the phase velocity value $C_{phase}$ by using Expression (1) above. As explained herein, the signal processing function 131 calculates the phase velocity value at the sampling point on the scanning line B, by using the phases at the sampling points on the scanning lines A to C, for example. Similarly, for example, the signal processing function 131 calculates a phase velocity value at the sampling point on the scanning line C, by using the phases at the sampling points on the scanning lines B to D. Further, for example, the signal processing function 131 calculates a phase velocity value at the sampling point on the scanning line D, by using the phases at the sampling points on the scanning lines C to E.

As explained above, the signal processing function 131 calculates the phase velocity value at each of the sampling points. The results illustrated in FIG. 4 are merely examples. For instance, the sampling points used for the calculations and the positions to which the calculated phase velocity values are assigned may be changed as appropriate. For example, the signal processing function 131 may calculate a phase velocity value by using the phases at four sampling points on the scanning lines A to D and assign the calculated phase velocity value to the middle point between the sampling points on the scanning lines B and C. Alternatively, for example, the signal processing function 131 may calculate a phase velocity value by using the phases at two sampling points on the scanning lines A and B and assign the calculated phase velocity value to the middle point between the sampling points on the scanning lines A and B. In other words, the phase velocity values calculated by the signal processing function 131 may be assigned to an arbitrary phase-velocity-value calculating position.

The signal processing function 131 calculates an index value that indicates a change amount of the calculated phase velocity values in the frequency direction (hereinafter, "variance of the phase velocity values") and that is not dependent on any physical model related to viscoelasticity. In other words, the signal processing function 131 calculates the index value indicating variance of the phase velocity values without using any physical model related to viscoelasticity. For example, the signal processing function 131 calculates the index value indicating the variance of the phase velocity values without performing a fitting process to any physical model related to viscoelasticity. In an example, the signal processing function 131 calculates a slope of a distribution of the phase velocity values, as the index value indicating the variance of the phase velocity values. In other words, the signal processing function 131 calculates the index value by using a frequency/phase velocity distribution calculated by analyzing the shear wave.

Figure 5:
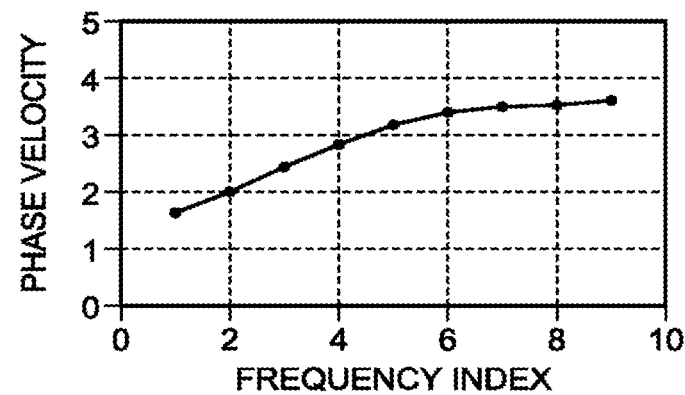
FIG. 5 is a drawing for explaining a process of calculating index values performed by the ultrasound diagnosis apparatus according to the first embodiment.

FIG. 5 is a drawing for explaining the process of calculating index values performed by the ultrasound diagnosis apparatus according to the first embodiment. FIG. 5 illustrates a chart (a distribution of phase velocity values) obtained by plotting phase velocity values at a sampling point on the scanning line B for mutually-different frequencies. In other words, the phase velocity values plotted in FIG. 5 are values calculated by using the phases at the sampling points on the scanning lines A, B, and C. In FIG. 5, the horizontal axis corresponds to a frequency index, whereas the vertical axis corresponds to the phase velocity values. The frequency index is an index indicating the frequencies used for calculating the phase velocity values. The magnitude of each of the values of the frequency index corresponds to the magnitude of the frequency.

As illustrated in FIG. 5, the signal processing function 131 plots the phase velocity values $C_{phase}$ at the sampling point on the scanning line B calculated by using Expression (1) in correspondence with the mutually-different frequency indexes and further calculates a slope from the plotted distribution of phase velocity values (hereinafter, "phase velocity distribution"). For example, the signal processing function 131 calculates the slope of the phase velocity distribution at the sampling point on the scanning line B, by performing a polynomial fitting process on an arbitrary frequency section in the phase velocity distribution. As the arbitrary frequency section, it is desirable to select a frequency section in which the shear wave 12 is more dominant that respiration, pulsation, body movements, and the like.

In this manner, the signal processing function 131 calculates the slope of the phase velocity distribution at the sampling point on the scanning line B, as an index value. Further, for each of the other sampling points, the signal processing function 131 similarly calculates the slope of the phase velocity distribution at the sampling point as an index value. In other words, by analyzing the detected shear wave, the signal processing function 131 calculates the index value that indicates the viscosity within the object and that is not dependent on any physical model related to viscoelasticity. The results illustrated in FIG. 5 are merely example. For instance, possible methods for calculating the slope of the phase velocity distribution are not limited to the method using the polynomial fitting process. As another method for calculating the slope of the phase velocity distribution, for example, a first-order approximation process may be performed in an arbitrary frequency section so as to calculate the slope thereof. Alternatively, for example, a logarithm fitting process of an arbitrary frequency section may be applied. In that situation, after the fitting process is performed, a differential coefficient at a certain frequency may be calculated as an index value. In other examples, any value may be calculated as an index value, as long as the index value makes it possible to evaluate the variance of the phase velocity values. Some of the other examples will be explained later.

Further, for instance, with reference to FIG. 5, the example is explained in which the index values are calculated by using the phase velocity values calculated with respect to the nine frequency components (frequency indexes); however, possible embodiments are not limited to this example. For instance, the signal processing function 131 may calculate an index value by using phase velocity values calculated with respect to an arbitrary number of frequency components. It should be noted that, however, it is desirable that the signal processing function 131 calculates an index value by using a phase velocity value calculated with respect to each of three or more frequency components, for the purpose of evaluating the variance of the phase velocity values.

Further, for instance, with reference to FIG. 5, the example is explained in which the chart is generated by plotting the phase velocity values in correspondence with the frequency indexes; however, possible embodiments are not limited to this example. It is also acceptable to generate a chart by plotting phase velocity values in correspondence with the frequency components.

The image processing function 132 is configured to generate an index image by assigning an attribute corresponding to the index value to a position corresponding to the calculation position of the phase velocity value. For example, the image processing function 132 generates index information in which the index values at the sampling points calculated by the signal processing function 131 are assigned to the sampling points. Further, by color-coding the generated index information and performing a scan convert process, the image processing function 132 generates an index image in which the index values at the sampling points are assigned to pixels.

For example, the image processing function 132 generates an index image 21 in which hues corresponding to the index values are assigned. In this situation, the attribute assigned in the index image 21 does not necessarily have to be hues. The assigned attribute may be luminosity or chroma, for example.

The output controlling function 133 is configured to display the index image. For example, the output controlling function 133 causes the display 103 to display the index image generated by the image processing function 132.

Figure 6:
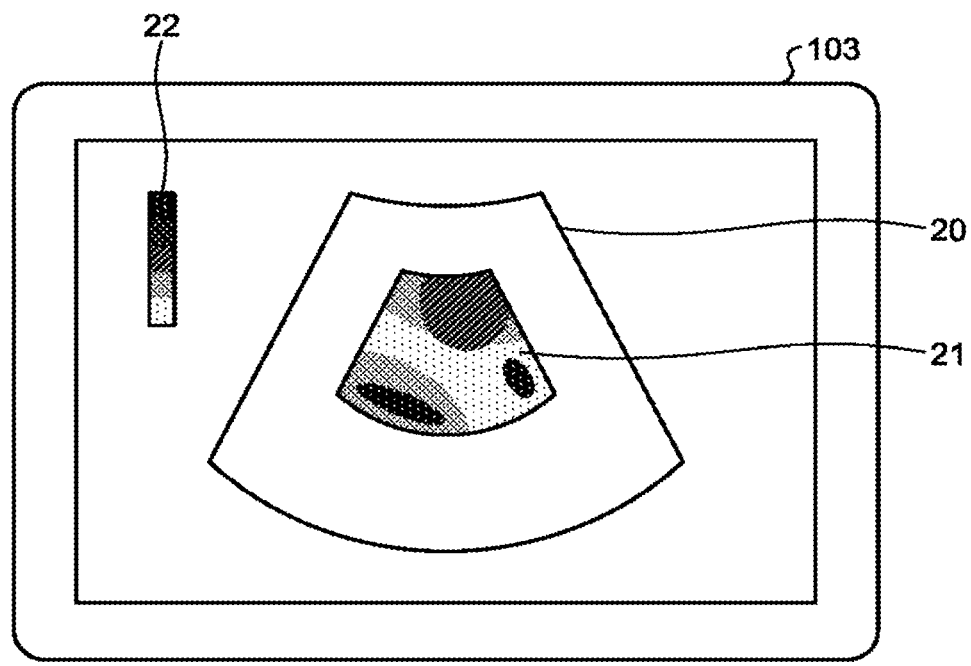
FIG. 6 is a drawing illustrating an example of an index image according to the first embodiment.

FIG. 6 is a drawing illustrating an example of the index image according to the first embodiment. FIG. 6 illustrates the index image 21 displayed over a B-mode image 20. The region for which the index image 21 is generated may arbitrarily be set by the operator.

As illustrated in FIG. 6, the output controlling function 133 causes the display 103 to display the index image 21 in which the index values at the sampling points are assigned to the pixels. In this situation, the output controlling function 133 causes the index image 21 to be displayed as being superimposed on the B-mode image 20 in the corresponding position. Further, the output controlling function 133 causes the display 103 to display a scale 22 indicating the correspondence between the index values of the pixels in the index image 21 and the hues assigned to the pixels.

As explained above, for example, the output controlling function 133 causes the index image 21 to be displayed in which the hues corresponding to the index values are assigned. Although FIG. 6 illustrates the example in which the index image 21 is displayed as being superimposed on the B-mode image 20, possible embodiments are not limited to this example. For instance, the index image 21 may be displayed alone, instead of being displayed as being superimposed on the B-mode image 20 or may be displayed simultaneously with another image such as the B-mode image 20. The simultaneous display will be explained later.

Figure 7:
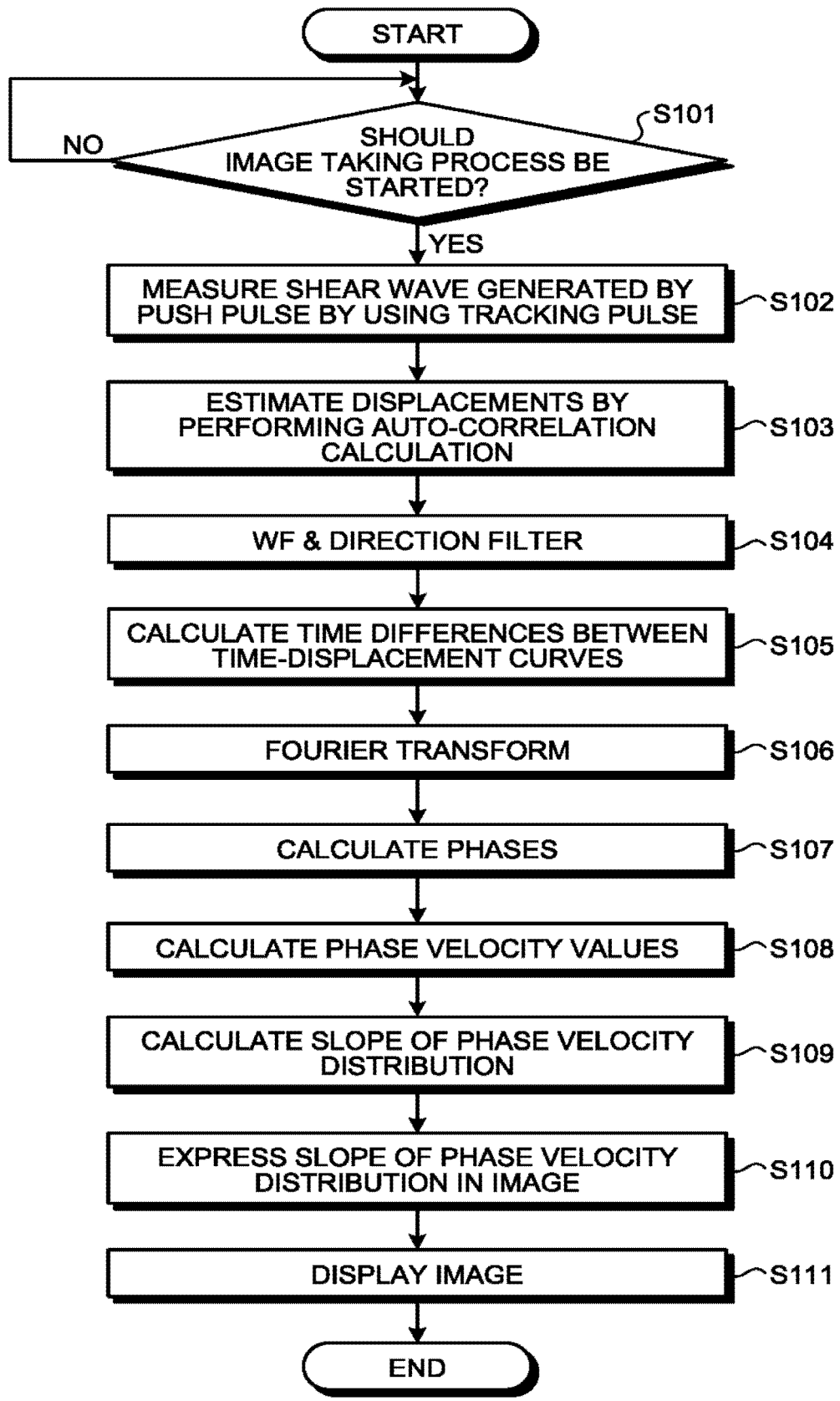
FIG. 7 is a flowchart illustrating a processing procedure performed by the ultrasound diagnosis apparatus according to the first embodiment.

FIG. 7 is a flowchart illustrating a processing procedure performed by the ultrasound diagnosis apparatus according to the first embodiment. The processing procedure illustrated in FIG. 7 is started, for example, when an instruction indicating that an index image taking process should be started, from the operator.

At step S101, the processing circuitry 130 judges whether or not an instruction has been received indicating that an index image taking process should be started. When having received an instruction indicating that an index image taking process should be started, the processing circuitry 130 starts the processes at step S102 and thereafter. When the judgment result at step S101 is in the negative, the processes at step S102 and thereafter are not started, and the processing functions of the processing circuitry 130 are in a standby state.

When the judgment result at step S101 is in the positive, the processing circuitry 130 measures, at step S102, a shear wave generated by the push pulse, by using the tracking pulse. For example, under the control of the processing circuitry 130, the transmission circuitry 110 causes the ultrasound probe 101 to transmit the tracking pulse multiple times for each of the plurality of scanning lines within the scanned region, the tracking pulse being used for measuring displacements caused by the push pulse.

At step S103, the signal processing function 131 estimates the displacements by using auto-correlation. For example, the signal processing function 131 estimates the displacement at each of the sampling points, by performing an auto-correlation calculation on the reflected-wave data of the tracking pulse 11 transmitted multiple times for each of the scanning lines A to F.

At step S104, the signal processing function 131 performs the filtering process by using a WF or a direction filter. As a result, for example, the signal processing function 131 estimates the displacements caused by the shear wave, while excluding components of the displacements caused by respiration, pulsation, body movements, and the like, from the estimated displacements.

At step S105, the signal processing function 131 calculates time differences between the time-displacement curves. For example, the signal processing function 131 calculates the time differences (the disparities) between the time-displacement curves on the basis of the propagation time periods of the shear wave 12.

At step S106, the signal processing function 131 performs a Fourier transform. For example, after shifting the analysis range in accordance with the time differences, the signal processing function 131 performs a window function processing process on the time-displacement curves and subsequently performs the Fourier transform.

At step S107, the signal processing function 131 calculates phases. For example, the signal processing function 131 calculates a phase for each of the frequencies, with respect to the sampling points obtained from the Fourier transform.

At step S108, the signal processing function 131 calculates phase velocity values. For example, the signal processing function 131 calculates a phase difference by using the phases calculated with respect to sampling points. After that, by using the phase difference, the distance L, and the frequency f, the signal processing function 131 calculates a phase velocity value at each of the sampling points.

At step S109, the signal processing function 131 calculates a slope of the phase velocity distribution, as an index value indicating the variance of the phase velocity values. For example, the signal processing function 131 calculates the slope of the phase velocity distribution at each of the sampling points, by performing a polynomial fitting process on an arbitrary frequency section of the phase velocity distribution at the sampling point.

At step S110, as an index image, the image processing function 132 expresses the slopes of the phase velocity distributions in an image. For example, the image processing function 132 generates index information in which the index values at the sampling points calculated by the signal processing function 131 are assigned to the sampling points. Further, the image processing function 132 generates an index image in which the index values at the sampling points are assigned to the pixels, by color-coding the generated index information and performing a scan convert process.

At step S111, the output controlling function 133 displays the index image. For example, the output controlling function 133 arranges the index image generated by the image processing function 132 to be displayed while being superimposed in the corresponding position within the B-mode image.

The procedure illustrated in FIG. 7 is merely an example. For instance, the filtering process at step S104 and the window function processing process at step S106 do not necessarily have to be performed.

As explained above, the ultrasound diagnosis apparatus according to the first embodiment is configured to calculate the index value that is not dependent on any physical model related to viscoelasticity, by using the frequency dependency of the velocity of the shear wave propagating through the viscous member. Accordingly, the ultrasound diagnosis apparatus according to the first embodiment is able to evaluate the viscosity of the tissue in the human body. Next, a relationship between the index values and an outline of the obtained displacements used by the ultrasound diagnosis apparatus according to the first embodiment will be explained, with reference to FIG. 8.

Figure 8:
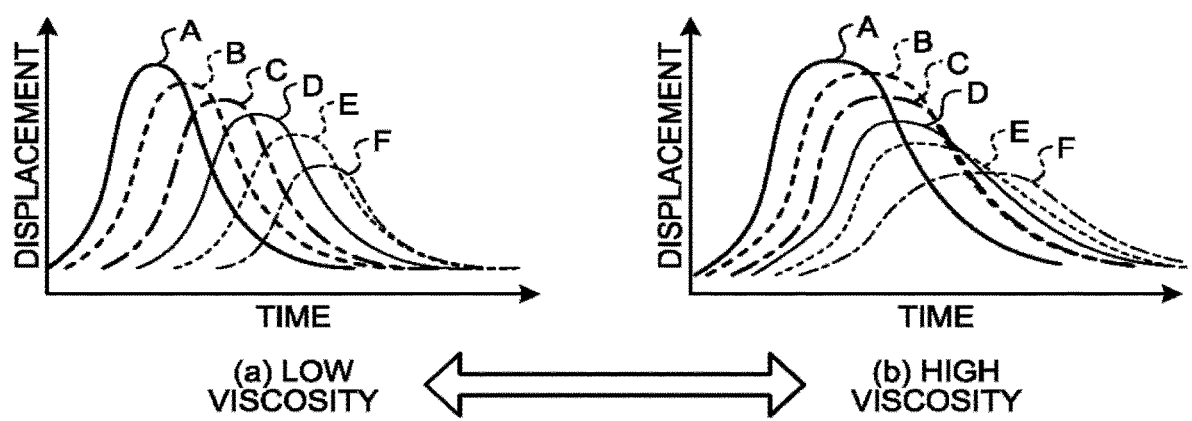
FIG. 8 is a drawing for explaining a relationship between index values and an outline of obtained displacements used by the ultrasound diagnosis apparatus according to the first embodiment.

FIG. 8 is a drawing for explaining the relationship between the index values and the outline of the obtained displacements used by the ultrasound diagnosis apparatus according to the first embodiment. FIG. 8(a) illustrates time-displacement curves of displacements occurring in a tissue having a lower level of viscosity, whereas FIG. 8(b) illustrates time-displacement curves of displacements occurring in a tissue having a higher level of viscosity. The illustrated displacements serve as a part of characteristics indicating the levels of viscosity, and possible embodiments are not limited to these examples. The different types of lines in FIG. 8 correspond to the time-displacement curves at the sampling points on the scanning lines A to F.

As illustrated in FIG. 8(a), in the time-displacement curves in the tissue having a low level of viscosity, although the displacement amount decreases in conjunction with the propagation of the shear wave, the shapes of the curves propagate without significant changes. In FIG. 8(a), for example, the shapes of the curves near the apexes of the time-displacement curves are substantially constant and appear to shift parallel to each other. When the shapes of the curves in the time-displacement curves are constant, for example, if the frequency is doubled, the phase difference (the slope in FIG. 4) is also doubled. In Expression (1) presented above, because the frequency is in the numerator, while the phase difference is in the denominator, the change amounts in the frequency and the phase difference cancel out each other, and the phase velocity value therefore does not change. In other words, it is understood that, when the level of viscosity is low, the phase velocity values are approximately constant, regardless of the frequencies.

In contrast, as illustrated in FIG. 8(b), in the time-displacement curves of the tissue having a high level of viscosity, the displacement amounts decrease in conjunction with the propagation of the shear wave, and also the shapes of the curves become broader in the time direction. In FIG. 8(b), for example, the longer is the distance from the source of the shear wave, the more gradual the rising and trailing of the time-displacement curves are, and also, the flatter the shapes of the curves near the apexes thereof become. When the shapes of the curves in the time-displacement curves become broader in the time direction, for example, even if the frequency is doubled, the phase difference is not necessarily doubled. Rather, the phase difference (a phase rotation amount) increases and becomes larger than the double. For this reason, the phase velocity values change while being dependent on the frequencies.

For these reasons, the ultrasound diagnosis apparatus according to the first embodiment is configured to calculate the index values of viscosity by expressing the changes in the shapes of the curves in the time-displacement curves corresponding to the viscosity levels as differences in the phase velocity values of the time-displacement curves. For example, the ultrasound diagnosis apparatus according to the first embodiment calculates a phase velocity value for each of a plurality of frequency components and further calculates the slope of a phase velocity distribution as an index value indicating the variance (a variance relationship) of the phase velocity values. Consequently, the ultrasound diagnosis apparatus according to the first embodiment is able to accurately evaluate the viscosity of the tissue in the human body. For example, the index value calculated by the ultrasound diagnosis apparatus according to the first embodiment exhibits a larger value when the viscosity is higher and exhibits a smaller value when the viscosity is lower.

Further, for example, the ultrasound diagnosis apparatus according to the first embodiment is configured to measure the index value from the reflected-wave data acquired from the patient P, without using any physical model related to viscoelasticity. For this reason, it is safe to say that the index value calculated by the ultrasound diagnosis apparatus according to the first embodiment is a qualitative value that is not dependent on any physical model. Further, because the index value is not dependent on any physical model, the index value is useful as a means for learning impacts (tendencies) made on patients' bodies by different levels of viscosity.

In other words, conventional models are obtained by substituting the characteristics (the viscoelasticity) of a human body with some equivalent circuits. These equivalent circuits do not necessarily show the human body. In contrast, the ultrasound diagnosis apparatus according to the first embodiment is configured to calculate the index value of the viscosity by performing the predetermined process on the measured values, without substituting the characteristics (the viscosity) of the human body with an equivalent circuit. Consequently, the ultrasound diagnosis apparatus according to the first embodiment is able to calculate the index value of the viscosity without performing the approximation process.

In the embodiment described above, for instance, the example is explained in which the various types of parameters such as the displacements, the phases, and the phase velocity values that were calculated are plotted in the charts, as appropriate; however, the various parameters do not necessarily have to be plotted. For instance, as long as it is possible to calculate the various types of parameters within the processing circuitry 130, it is not necessary to plot these parameters. However, when displaying a chart, the processing circuitry 130 may plot the various types of parameters in the chart, as appropriate, so that the display 103 displays the chart.

Second Embodiment

In a second embodiment, a process of expressing, in an image, a range equal to or longer than an attenuation distance of a shear wave will be explained. First, attenuation of a shear wave will be explained, with reference to FIG. 9.

FIG. 9 is a drawing for explaining the attenuation of a shear wave. FIG. 9 schematically illustrates the push pulse 10 and the tracking pulse 11 transmitted from the ultrasound probe 101. In FIG. 9, the arrow t corresponds to the time direction.

As illustrated in FIG. 9, the shear wave 12 generated by the push pulse 10 attenuates during the propagation. For this reason, for example, there may be some situations where, even if the shear wave 12 is detected on the scanning lines A to F, the shear wave 12 may not be detected on the scanning lines G to I, which are more distant. In those situations, even if a shear wave generated by using another push pulse is detected on the scanning lines G to I, some data is missing between the scanning line F and the scanning line G. When obtained data is expressed into an image while some of the data is missing, there is a possibility that the image quality may be degraded.

To cope with this situation, in the second embodiment, a process for expressing, in an image, a range equal to or longer than an attenuation distance of a shear wave will be explained.

The ultrasound diagnosis apparatus according to the second embodiment has the same configuration as that of the ultrasound diagnosis apparatus illustrated in FIG. 1, except a part of the processes performed thereby is different. Thus, in the second embodiment, the differences from the first embodiment will primarily be explained. Explanations of some of the elements having the same functions as those explained in the first embodiment will be omitted.

The processing circuitry 130 according to the second embodiment is configured to arrange at least one position in adjacently-positioned scan ranges to be scanned in a duplicate manner, when detecting a shear wave in each of a plurality of mutually-different scan ranges.

FIG. 10 is a drawing for explaining a process performed by the processing circuitry 130 according to the second embodiment. FIG. 10 schematically illustrates push pulses 10 and 30 and tracking pulses 11 and 31 transmitted from the ultrasound probe 101. In FIG. 10, the arrow t corresponds to the time direction.

As illustrated in FIG. 10, under the control of the processing circuitry 130, the transmission circuitry 110 causes the tracking pulse 11 to be transmitted multiple times for each of the scanning lines A to F, the tracking pulse 11 being used for measuring the displacements caused by the push pulse 10. Further, the transmission circuitry 110 causes the tracking pulse 31 to be transmitted multiple times for each of the scanning lines D to I, the tracking pulse 31 being used for measuring the displacements caused by the push pulse 30. In this manner, when performing the scanning process by using the two mutually-different shear waves 12 and 32, the processing circuitry 130 arranges the scanning lines D to F to be scanned in a duplicate manner, among the scanning lines A to F used for measuring the shear wave 12 and the scanning lines D to I used for measuring the shear wave 32.

As explained above, when detecting the shear wave in each of the plurality of mutually-different scan ranges, the processing circuitry 130 arranges at least one of the scanning lines in the adjacently-positioned scan ranges to be scanned in a duplicate manner.

The processing circuitry 130 is configured to join together the phases calculated in the positions included in the adjacently-positioned scan ranges, by using the phases in the positions scanned in the duplicate manner.

Figure 11:
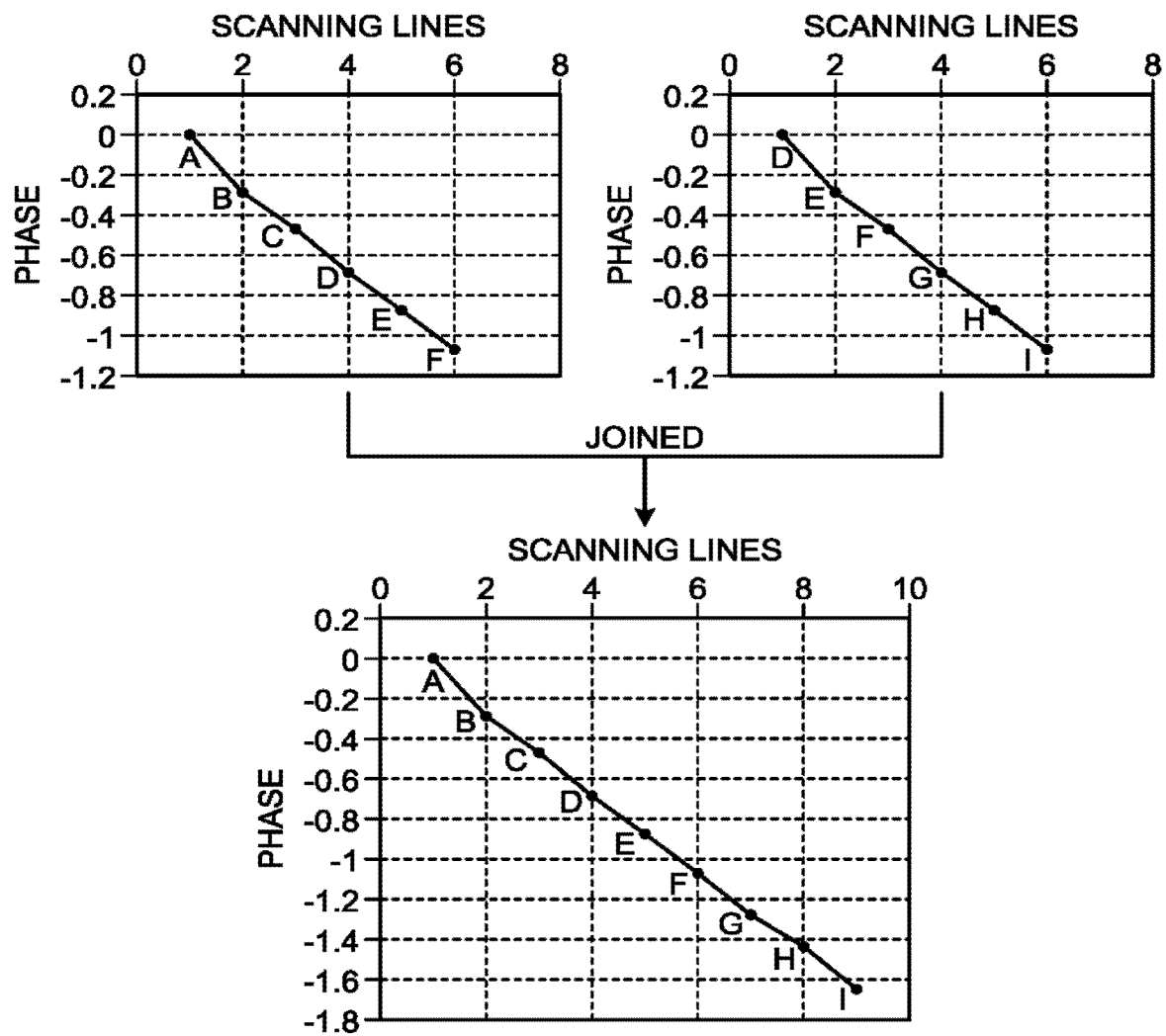
FIG. 11 is a drawing for explaining another process performed by the processing circuit according to the second embodiment.

FIG. 11 is a drawing for explaining another process performed by the processing circuitry 130 according to the second embodiment. FIG. 11 schematically illustrates a situation in which the phases at the sampling points calculated by using the two shear waves 12 and 32 are joined together. The chart in the top left section of FIG. 11 illustrates the phases at the sampling points on the scanning lines A to F calculated by using the shear wave 12 illustrated in FIG. 10. Also, the chart in the top right section of FIG. 11 illustrates the phases at the sampling points on the scanning lines D to I calculated by using the shear wave 32 illustrated in FIG. 10. Further, the chart in the bottom section of FIG. 11 illustrates a result obtained by joining together the phases at the sampling points calculated by using the shear waves 12 and 32.

As illustrated in the top left section of FIG. 11, in the processing circuitry 130, the signal processing function 131 calculates the phases at the sampling points on the scanning lines A to F by performing a Fourier transform on the shear wave 12. After that, the signal processing function 131 calculates the phase differences among the scanning lines A to F, by using the phase at the sampling point on the scanning line A as a reference (zero). Further, as illustrated in the top right section of FIG. 11, the signal processing function 131 calculates the phases at the sampling points on the scanning lines D to I, by performing a Fourier transform on the shear wave 32. After that, the signal processing function 131 calculates the phase differences among the scanning lines D to I, by using the phase at the sampling point on the scanning line D as a reference (zero). As explained herein, the two charts use the mutually-different phases as the reference. In this situation, because the process of calculating the phases is the same as that in the first embodiment, the explanation thereof will be omitted.

In the present example, between these two charts, the sampling points on the scanning lines D, E, and F are the same as each other. Thus, as illustrated in the chart in the bottom section of FIG. 11, the signal processing function 131 joins the phases at the sampling points on the scanning lines A to F with the phases at the sampling points on the scanning lines D to I, by using the phases at the sampling points on the scanning lines D, E, and F. For example, the signal processing function 131 calculates, between the two charts, the difference in the phase at the sampling point on the scanning line D, the difference in the phase at the sampling point on the scanning line E, and the difference in the phase at the sampling point on the scanning line F. The signal processing function 131 further calculates an average value of the calculated differences. After that, the signal processing function 131 joins together the phases at the sampling points on the scanning lines G to I so as to be fitted to the chart in the top left section, by adding the calculated average value to each of the phases at the sampling points on the scanning lines G to I.

As explained above, the processing circuitry 130 joins together the phases calculated in the positions included in the adjacently-positioned scan ranges, by using the phase in the position scanned in the duplicate manner. With this arrangement, the signal processing function 131 is able to similarly handle the phases of the scanning lines A to I by performing the process described in the first embodiment.

As explained above, when detecting the shear wave in each of the plurality of mutually-different scan ranges, the ultrasound diagnosis apparatus according to the second embodiment is configured to arrange at least one of the positions in the adjacently-positioned scan ranges to be scanned in the duplicate manner. After that, the ultrasound diagnosis apparatus is configured to join together the phases calculated in the positions included in the adjacently-positioned scan ranges, by using the phases in the positions scanned in the duplicate manner. Consequently, the ultrasound diagnosis apparatus is able to express, in the image, the range equal to or longer than the attenuation distance of the shear wave, with a high level of image quality.

The description above merely explains certain examples. For instance, in the description above, the example is explained in which the three scanning lines are scanned in the duplicate manner; however, possible embodiments are not limited to this example. The number of scanning lines to be scanned in a duplicate manner may arbitrarily be set. It should be noted, however, that it is desirable to scan at least one of the scanning lines in a duplicate manner.

Other Embodiments

The present disclosure may be carried out in various other embodiments besides the embodiments described above.
<An Analyzing Apparatus>
In the embodiments above, for example, the ultrasound diagnosis apparatus is explained as an example of the analyzing apparatus; however, possible embodiments are not limited to this example. For instance, it is possible to have the processes executed by an arbitrary apparatus, as long as it is possible to detect a shear wave propagating in an object and information is available to an extent that makes it possible to obtain the time-displacement curve.

In that situation, for example, an analyzing apparatus according to another embodiment includes the processing circuitry 130. The processing circuitry 130 is configured to detect a shear wave propagating in an object with respect to each of a plurality of positions arranged along the propagation direction of the shear wave. The processing circuitry 130 is configured to calculate the phase of each of a plurality of frequency components included in the detected shear wave. By using the phases calculated with respect to the positions, the processing circuitry 130 is configured to calculate a phase velocity value for each of the frequency components. The processing circuitry 130 is configured to calculate an index value that indicates variance of the calculated phase velocity values and that is not dependent on any physical model related to viscoelasticity. Consequently, the analyzing apparatus according to said another embodiment is able to accurately evaluate the viscosity of the tissue in the human body.

An Index Value Indicating Variance of Phase Differences
Further, for example, in the embodiments above, the example is explained in which the phase velocity values at the sampling points are calculated so as to calculate the index value indicating the variance of the calculated phase velocity values; however, possible embodiments are not limited to this example. For instance, the signal processing function 131 may calculate an index value indicating variance of phase differences.

In that situation, an ultrasound diagnosis apparatus according to yet another embodiment includes the processing circuitry 130. The processing circuitry 130 is configured to detect a shear wave propagating in an object with respect to each of a plurality of positions arranged along the propagation direction of the shear wave. The processing circuitry 130 is configured to calculate a phase of each of a plurality of frequency components included in the detected shear wave. By using the phases calculated with respect to the positions, the processing circuitry 130 is configured to calculate a phase difference for each of the frequency components. The processing circuitry 130 is configured to calculate an index value that indicates variance of the calculated phase differences and that is not dependent on any physical model related to viscoelasticity. In other words, the signal processing function 131 is configured to calculate the index value, by using a frequency/phase difference distribution calculated by analyzing the shear wave.

In the present example, as the index indicating the variance of the phase differences, the processing circuitry 130 calculates a slope of the phase differences, for example. More specifically, the processing circuitry 130 may calculate the slope illustrated in FIG. 4 as the index value as described above. Consequently, the ultrasound diagnosis apparatus according to said yet another embodiment is able to evaluate the viscosity of a tissue in the human body, by using the phase differences as the index. Further, in that situation, the processing circuitry 130 does not necessarily have to calculate the phase velocity values. In other words, the processing circuitry 130 according to the present embodiment is configured to calculate the index indicating the variance of the phase differences or the phase velocity values without using any physical model related to viscoelasticity. For example, the processing circuitry 130 calculates the index value indicating the variance of the phase differences or the phase velocity values, without performing a fitting process to a physical model related to viscoelasticity.

Imaging of the Phase Velocity Values
Further, for example, an ultrasound diagnosis apparatus according to yet another embodiment may perform an imaging process on a phase velocity value corresponding to a specific frequency.

In that situation, the ultrasound diagnosis apparatus according to said yet another embodiment includes the processing circuitry 130. The processing circuitry 130 is configured to detect a shear wave propagating in an object with respect to each of a plurality of positions arranged along the propagation direction of the shear wave. The processing circuitry 130 is configured to calculate a phase corresponding to a specific frequency component included in the detected shear wave. By using the phases calculated with respect to the positions, the processing circuitry 130 is configured to calculate a phase velocity value. By using the calculated phase velocity value as an index value, the processing circuitry 130 is configured to generate an index image by assigning an attribute corresponding to the index value to a position corresponding to the calculation position of the phase velocity value. Consequently, the ultrasound diagnosis apparatus according to said yet another embodiment is able to perform the imaging process on the phase velocity value corresponding to the specific frequency.

In that situation, the processing circuitry 130 does not need to calculate phase velocity values with respect to a plurality of frequency components, unlike in the embodiments described above. In other words, the ultrasound diagnosis apparatus may calculate the phase velocity value only with respect to the specific frequency component and generate an image in which a pixel value corresponding to the phase velocity value is assigned.

Imaging of Phase Differences

Further, for example, the ultrasound diagnosis apparatus according to yet another embodiment may perform an imaging process on a phase difference corresponding to a specific frequency.

For example, an ultrasound diagnosis apparatus according to said yet another embodiment includes the processing circuitry 130. The processing circuitry 130 is configured to detect a shear wave propagating in an object, with respect to each of a plurality of positions arranged along the propagation direction of the shear wave. The processing circuitry 130 is configured to calculate a phase corresponding to a specific frequency component included in the detected shear wave. The processing circuitry 130 is configured to calculate a phase difference by using the phases calculated with respect to the positions. By using the calculated phase difference as an index value, the processing circuitry 130 is configured to generate an index image by assigning an attribute corresponding to the index value to a position corresponding to the calculation position of the phase difference. Consequently, the ultrasound diagnosis apparatus according to said yet another embodiment is able to perform the imaging process on the phase difference corresponding to the specific frequency.

In that situation, the processing circuitry 130 does not need to calculate phase differences with respect to a plurality of frequency components, unlike in the embodiments described above. In other words, the ultrasound diagnosis apparatus may calculate the phase difference only with respect to the specific frequency and generate the image in which the pixel value corresponding to the phase difference is assigned.

A Measuring Process Performed on the Index Image

Further, for example, the index image generated by any of the ultrasound diagnosis apparatuses explained in the embodiments above may be used for a measuring process.

Figure 12:
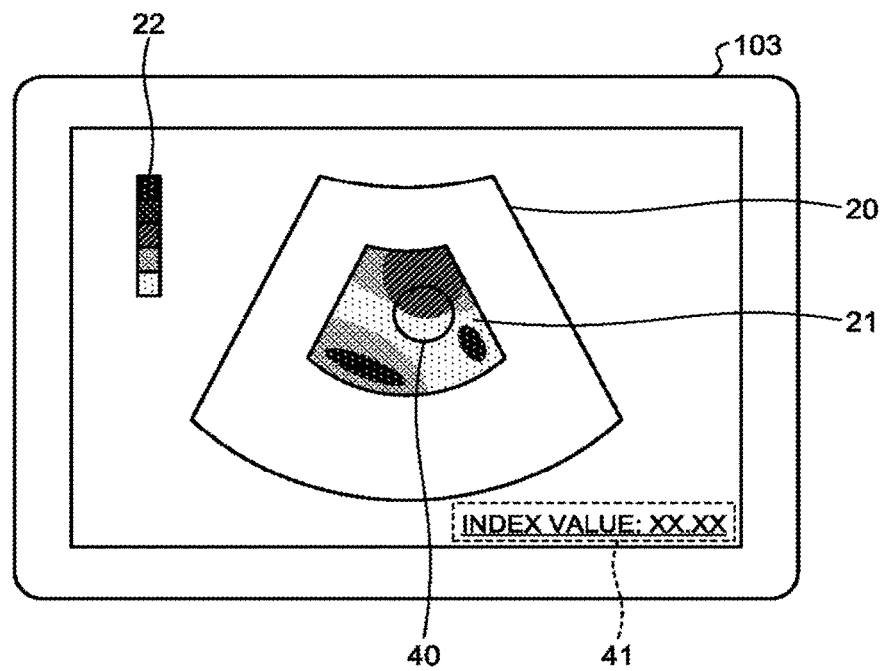
FIG. 12 is a drawing for explaining a measuring process performed by an ultrasound diagnosis apparatus according to another embodiment.

FIG. 12 is a drawing for explaining a measuring process performed by an ultrasound diagnosis apparatus according to yet another embodiment. FIG. 12 illustrates the index image 21 displayed over the B-mode image 20. In FIG. 12, a measuring Region Of Interest (ROI) 40 is set in the index image 21 in response to an instruction from the operator.

As illustrated in FIG. 12, when the measuring ROI 40 has been set in response to the instruction from the operator, the processing circuitry 130 calculates an average value of index values included in the set measuring ROI 40. Further, the processing circuitry 130 displays the calculated average value "XX.XX" in a region 41, as a value of the measuring ROI 40.

As explained above, the processing circuitry 130 is configured to calculate a statistic value that uses the index values included in the region of interest set in the index image 21. The statistic value calculated by the processing circuitry 130 does not necessarily have to be an average value and may be, for example, a median value, a variance value, a standard deviation, or the like. Further, the processing circuitry 130 may output the statistic value to a report generating computer program. For example, to arrange the measured value and the index image 21 to be reflected in a report of the patient P, the processing circuitry 130 may output the measured value and the index image 21 to a report generating computer program configured to generate the report.

A Simultaneous Display with Another Image

Further, for example, the index image 21 generated by any of the ultrasound diagnosis apparatuses according to the embodiments described above may be displayed by the display 103 simultaneously with another image.

The processing circuitry 130 is configured to generate at least one selected from between an image (a B-mode image) indicating a tissue characteristic within an object and an image based on a propagation time period it takes for a shear wave to propagate to each of a plurality of positions and to further display the generated image simultaneously with an index image. For example, the processing circuitry 130 generates and displays a firmness image as the image based on the propagation time period it takes for the shear wave to propagate to each of the plurality of positions.

Figure 13:
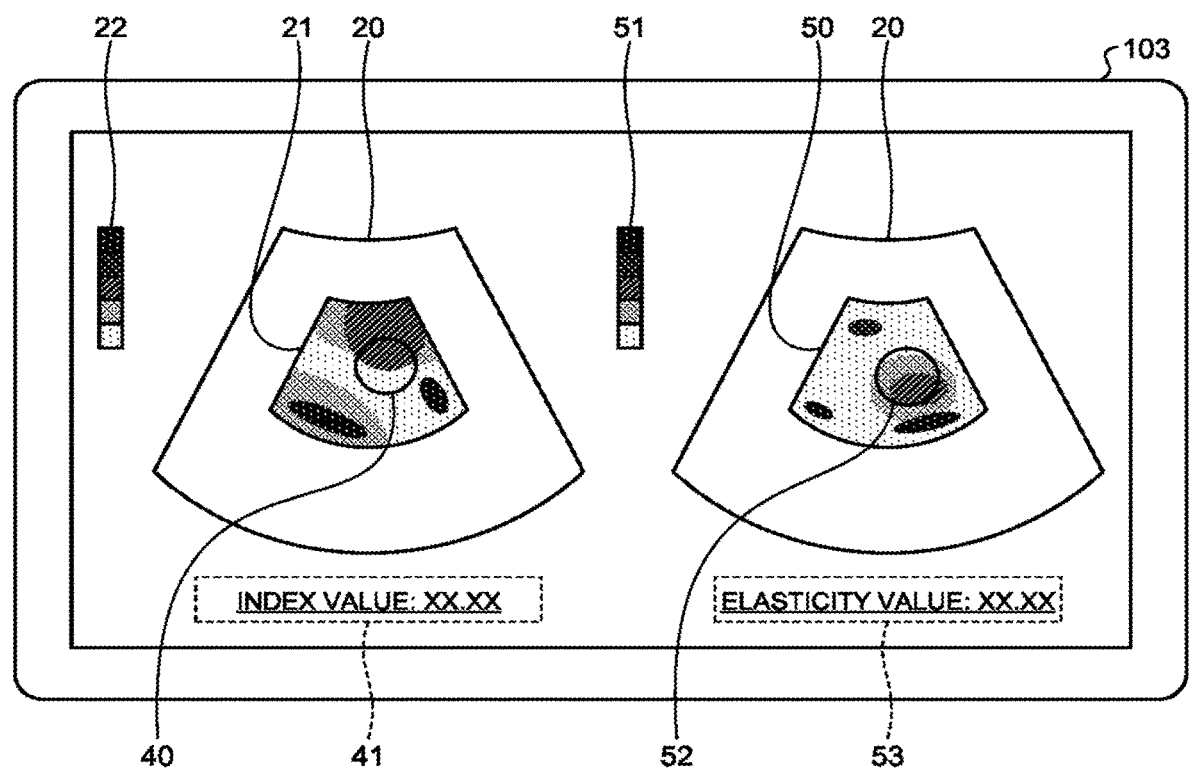
FIG. 13 is a drawing for explaining a simultaneous display realized by an ultrasound diagnosis apparatus according to yet another embodiment.

FIG. 13 is a drawing for explaining a simultaneous display realized by an ultrasound diagnosis apparatus according to yet another embodiment. FIG. 13 illustrates the index image 21 displayed over the B-mode image 20 and a firmness image 50 displayed in another B-mode image 20. In FIG. 13, the measuring ROI 40 is set in the index image 21, while a measuring ROI 52 is set in the firmness image 50. A scale 51 is a scale indicating the correspondence between moduli of elasticity of the pixels in the firmness image 50 and the hues assigned to the pixels.

As illustrated in FIG. 13, the processing circuitry 130 generates the firmness image 50. For example, the processing circuitry 130 calculates a propagation time period of the shear wave on the basis of a mutual correlation among the time-displacement curves obtained in FIG. 3 and further calculates a propagation velocity value of the shear wave, on the basis of the calculated propagation time period and the distance between sampling points. Further, the processing circuitry 130 calculates a modulus of elasticity obtained by converting the calculated propagation velocity value into a Young's modulus. The processing circuitry 130 generates the firmness image 50 by assigning a pixel value by using the calculated modulus of elasticity as an index of firmness.

After that, the processing circuitry 130 arranges the generated firmness image 50 to be displayed so as to be superimposed in a corresponding position within the B-mode image 20 and to be displayed simultaneously with the index image 21. Further, the processing circuitry 130 calculates an average value of the moduli of elasticity included in the measuring ROI 52 and further displays the calculated average value "XX.XX" in a region 53, as an elasticity value of the measuring ROI 52.

As explained above, the processing circuitry 130 may cause the display 103 to display another image such as the firmness image 50 simultaneously with the index image 21. The image simultaneously displayed with the index image 21 may be an image other than the firmness image 50.

For example, as the image based on the propagation time period, the processing circuitry 130 may be configured to generate at least one selected from among: an image obtained by assigning a pixel value corresponding to the propagation time period; an image (the firmness image 50) obtained by assigning a pixel value corresponding to a firmness level calculated from the propagation time period; an image indicating positions having substantially the same propagation time period as each other; and an image obtained by assigning a pixel value corresponding to a variance value of the propagation time period and to further display the generated image simultaneously with an index image.

Further, for example, the index image 21 and the firmness image 50 do not necessarily have to be displayed as being superimposed on the B-mode image 20. Further, the measuring ROI 52 may automatically be set in accordance with the setting of the measuring ROI 40. In other words, when a first region of interest is set in one of the images simultaneously displayed, the processing circuitry 130 may set a second region of interest in such a position in the other of the images that corresponds to the first region of interest and may calculate a statistic value that uses values included in the regions of interest, with respect to each of the first and the second regions of interest that were set.

Further, for instance, the images that are simultaneously displayed do not necessarily have to be the two images illustrated in FIG. 13, but may be four images, for example. For instance, the processing circuitry 130 is able to display an image in which pixel values corresponding to an arbitrary parameter calculated in any of the embodiments described above are assigned.

Figure 14:
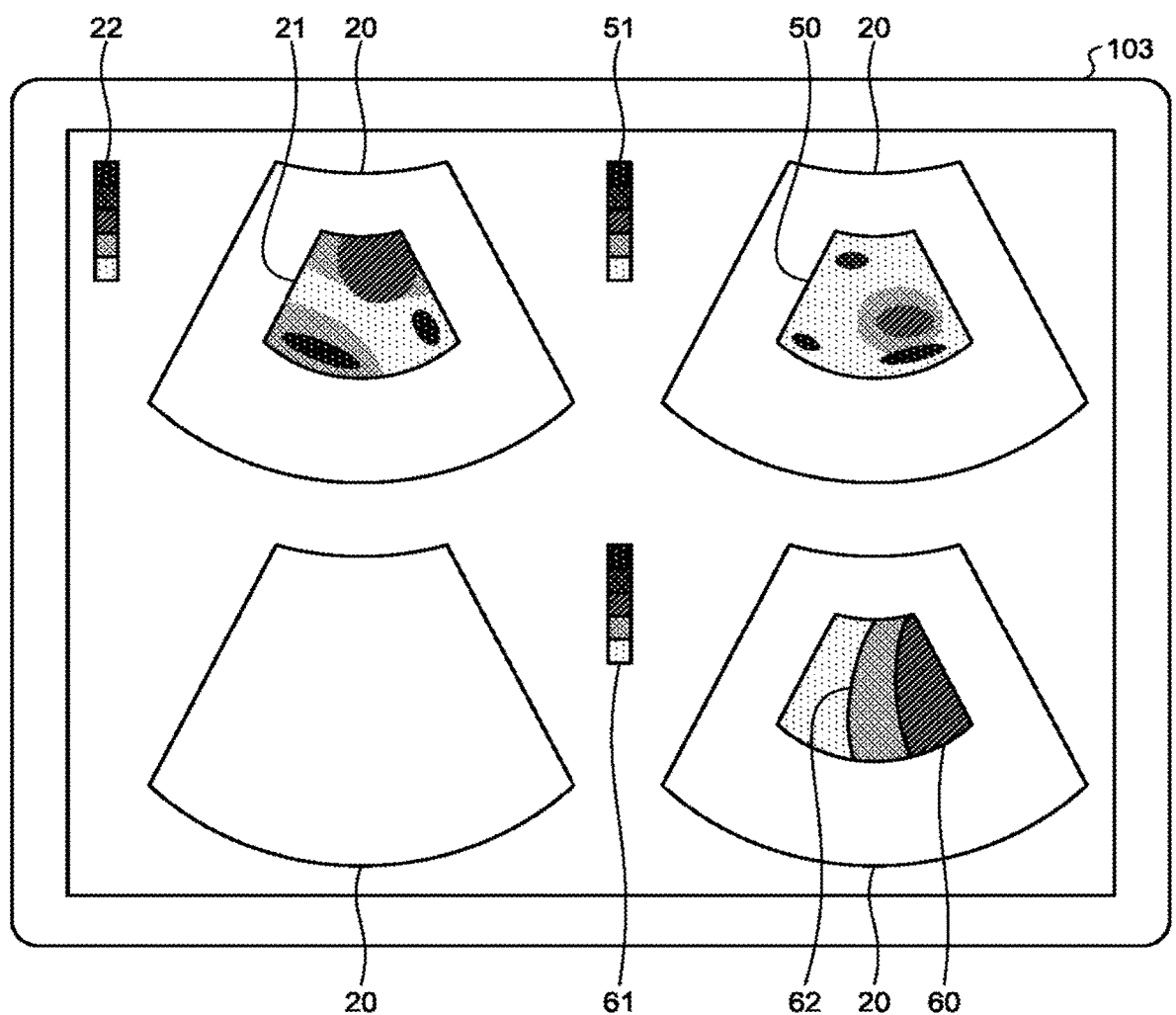
FIG. 14 is a drawing for explaining another simultaneous display realized by an ultrasound diagnosis apparatus according to yet another embodiment.

FIG. 14 is a drawing for explaining another simultaneous display realized by an ultrasound diagnosis apparatus according to yet another embodiment. FIG. 14 illustrates a B-mode image 20 on which nothing is superimposed and a propagation time period image 60 superimposed on the B-mode image 20, in addition to the index image 21 and the firmness image 50 illustrated in FIG. 13.

As illustrated in FIG. 14, for example, the processing circuitry 130 generates and displays the propagation time period image 60, as an image indicating positions having substantially the same propagation time periods as each other. The propagation time period image 60 is an image in which mutually-the-same pixel value is assigned to such positions that have substantially the same propagation time periods as each other at the sampling points and serves as an index of reliability related to the acquired information about displacements. The reason is that, when the propagation time periods of the displacements are substantially uniform within an image, it is considered that the displacements propagate within the image in a stable manner, which means that the reliability of the acquired information about the displacements is high. On the contrary, when the propagation time periods of the displacements are not uniform within an image, it is considered that the displacements did not propagate due to a certain cause, which means that the reliability is low (there is a high possibility that an artifact has occurred). In the propagation time period image 60, the pixel values do not necessarily have to be assigned to all the pixels. For instance, as indicated with the line 62 in FIG. 14, the positions having substantially the same propagation time periods as each other may be displayed at predetermined intervals (i.e., a display using a method similar to a contour map). Further, the processing circuitry 130 causes the display 103 to display a scale 61 indicating the correspondence between the index values of the pixels in the propagation time period image 60 and the hues assigned to the pixels.

Calculating an Index Value by Using a Two-Dimensional Fourier Transform

In the embodiments above, the example is explained in which the index value indicating the viscosity is calculated by performing the Fourier transform in the time direction on the temporal change of the displacements (e.g., the time-displacement curves in FIG. 3); however, possible embodiments are not limited to this example. For instance, it is also possible to calculate an index value indicating viscosity by performing a two-dimensional Fourier transform (2D-FFT) on a distribution of displacements (hereinafter, "displacement distribution") in time-space directions.

In other words, the signal processing function 131 performs the two-dimensional Fourier transform in the time direction and the space direction on the displacement distribution in the time-space directions. Further, the signal processing function 131 calculates a phase velocity value for each frequency, on the basis of a result of the two-dimensional Fourier transform. After that, the signal processing function 131 calculates the index value indicating the viscosity, by using the phase velocity value corresponding to each frequency.

Figure 15A:
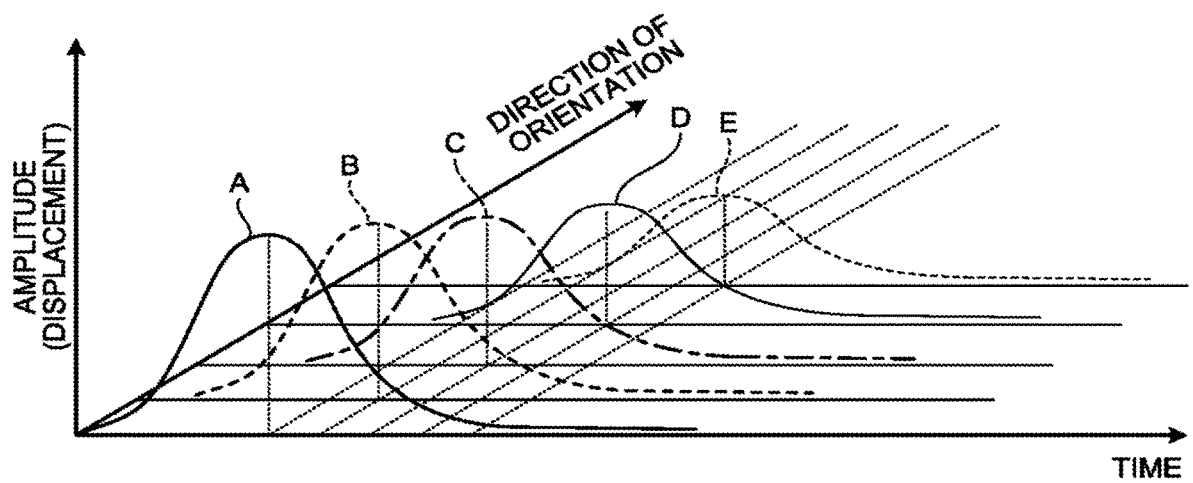
FIGS. 15A and 15B are drawings illustrating examples of distributions of displacements in time-space directions according to yet another embodiment.
Figure 15B:
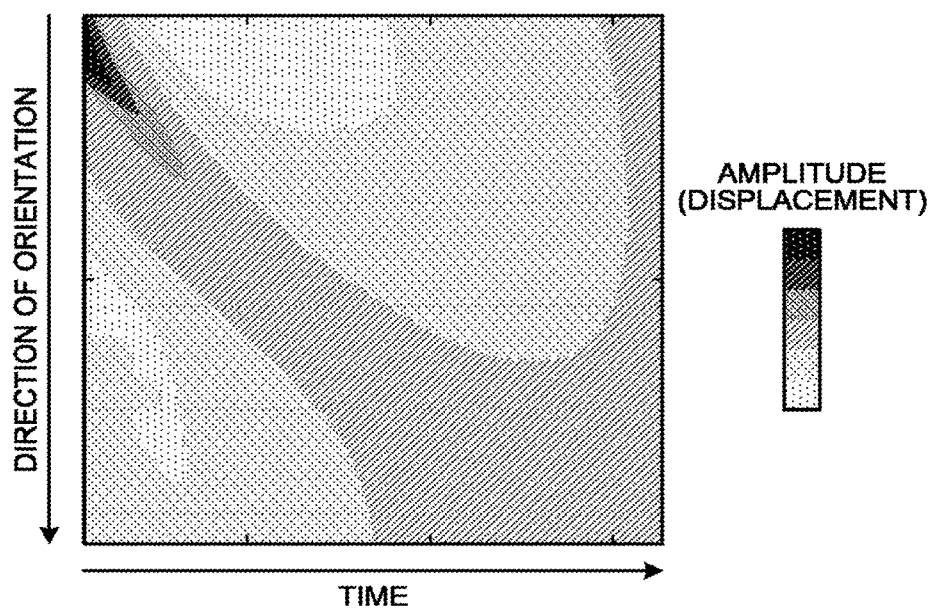
Figure 16:
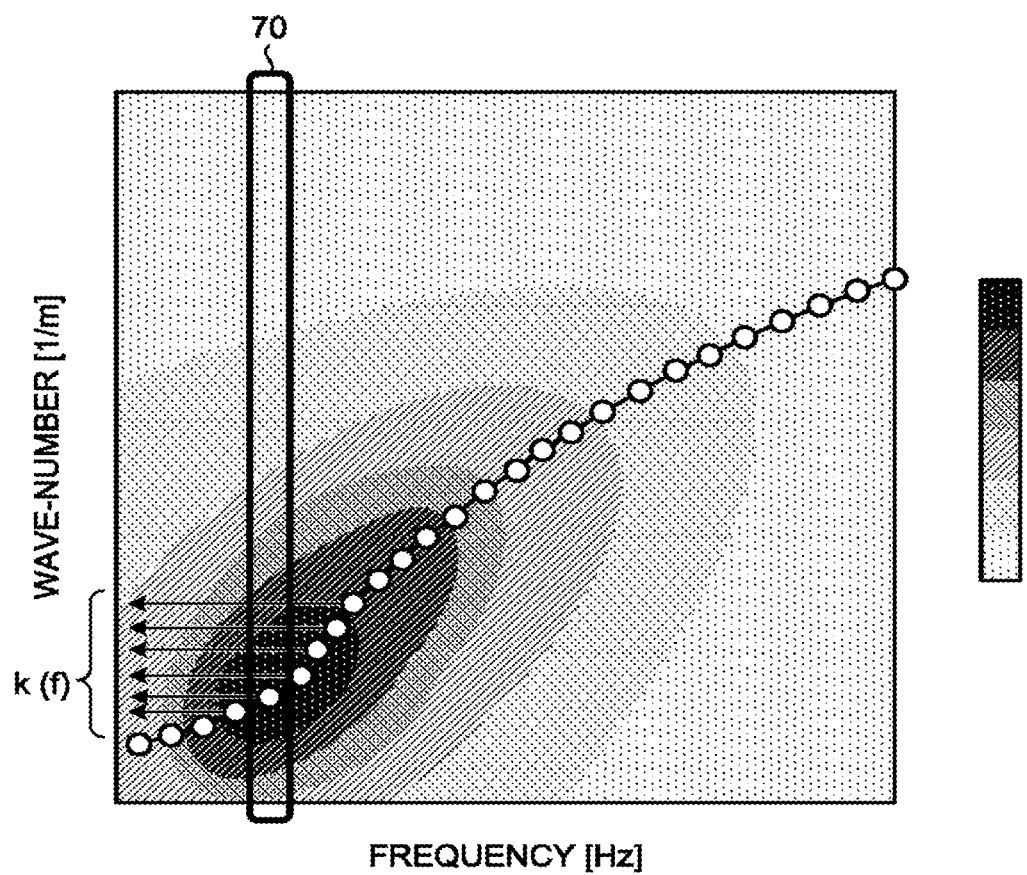
FIG. 16 is a drawing illustrating an example of a distribution of power spectra obtained by performing a two-dimensional Fourier transform according to yet another embodiment.

FIGS. 15A, 15B, and 16 are drawings illustrating examples of displacement distributions in time-space directions according to yet another embodiment. In FIG. 15A, the horizontal direction corresponds to the time direction, whereas the vertical direction corresponds to the magnitude of amplitudes (displacements), while the depth direction corresponds to the direction of orientation. Further, in FIG. 15B, the horizontal direction corresponds to the time direction, whereas the vertical direction corresponds to the direction of orientation, while changes of colors correspond to the magnitude of amplitudes (displacements). FIGS. 15A and 15B illustrate the displacement distribution on which the two-dimensional Fourier transform is performed by using the mutually-different display modes, but the illustrated contents are substantially the same as each other. FIG. 16 illustrates a distribution of power spectra (hereinafter, "power spectrum distribution") obtained by performing a two-dimensional Fourier transform.

As illustrated in FIGS. 15A and 15B, the signal processing function 131 performs a two-dimensional Fourier transform on the displacement distribution in the time-space directions. In this situation, the displacement distribution on which the two-dimensional Fourier transform is performed is expressed on the three axes extending in the time direction, the space direction (the direction of orientation), and the magnitude of displacements. More specifically, the signal processing function 131 performs the two-dimensional Fourier transform in the time direction and the space direction on the displacement distribution in the time-space directions illustrated in FIGS. 15A and 15B. As a result, the signal processing function 131 obtains the power spectrum distribution (see FIG. 16).

FIG. 16 is a drawing illustrating an example of the power spectrum distribution obtained by performing the two-dimensional Fourier transform according to said yet another embodiment. In FIG. 16, the horizontal direction corresponds to frequency [Hz], whereas the vertical direction corresponds to the wave-number [1/m], while changes of colors correspond to power spectra. In FIG. 16, the frequencies in the horizontal direction correspond to temporal frequencies, whereas the wave-numbers in the vertical direction correspond to spatial frequencies.

As illustrated in FIG. 16, the signal processing function 131 obtains a wave number k(f) at which the power spectrum exhibits a maximum value among the frequencies (the temporal frequencies). More specifically, the signal processing function 131 obtains the maximum value of the power spectrum distribution (corresponding to the region 70 in FIG. 16) in the wave-number direction observed when the frequency f is fixed, on the basis of the power spectrum distribution illustrated in FIG. 16. As a result, the signal processing function 131 obtains the maximum values (the small circles in FIG. 16) of the power spectrum corresponding to each of the frequencies f. After that, the signal processing function 131 obtains the wave-number k(f) corresponding to each of the obtained maxim values, from the power spectrum distribution.

After that, by using Expression (2) below, the signal processing function 131 calculates a phase velocity value C(f). For example, by using Expression (2), the signal processing function 131 calculates the phase velocity value C(f), for each of the frequencies f.

$$C(f) = \frac{\omega}{k(f)} = \frac{2\pi f}{k(f)} \quad (2)$$

After that, by using the phase velocity value C(f) for each of the frequencies f, the signal processing function 131 calculates an index value indicating viscosity. For example, as illustrated in FIG. 5, the signal processing function 131 calculates a slope of a frequency/phase velocity distribution as the index indicating the viscosity. In that situation, the calculated index value is assigned to the center position in the space direction of the displacement distribution on which the two-dimensional Fourier transform is performed (see FIG. 17).

Figure 17:
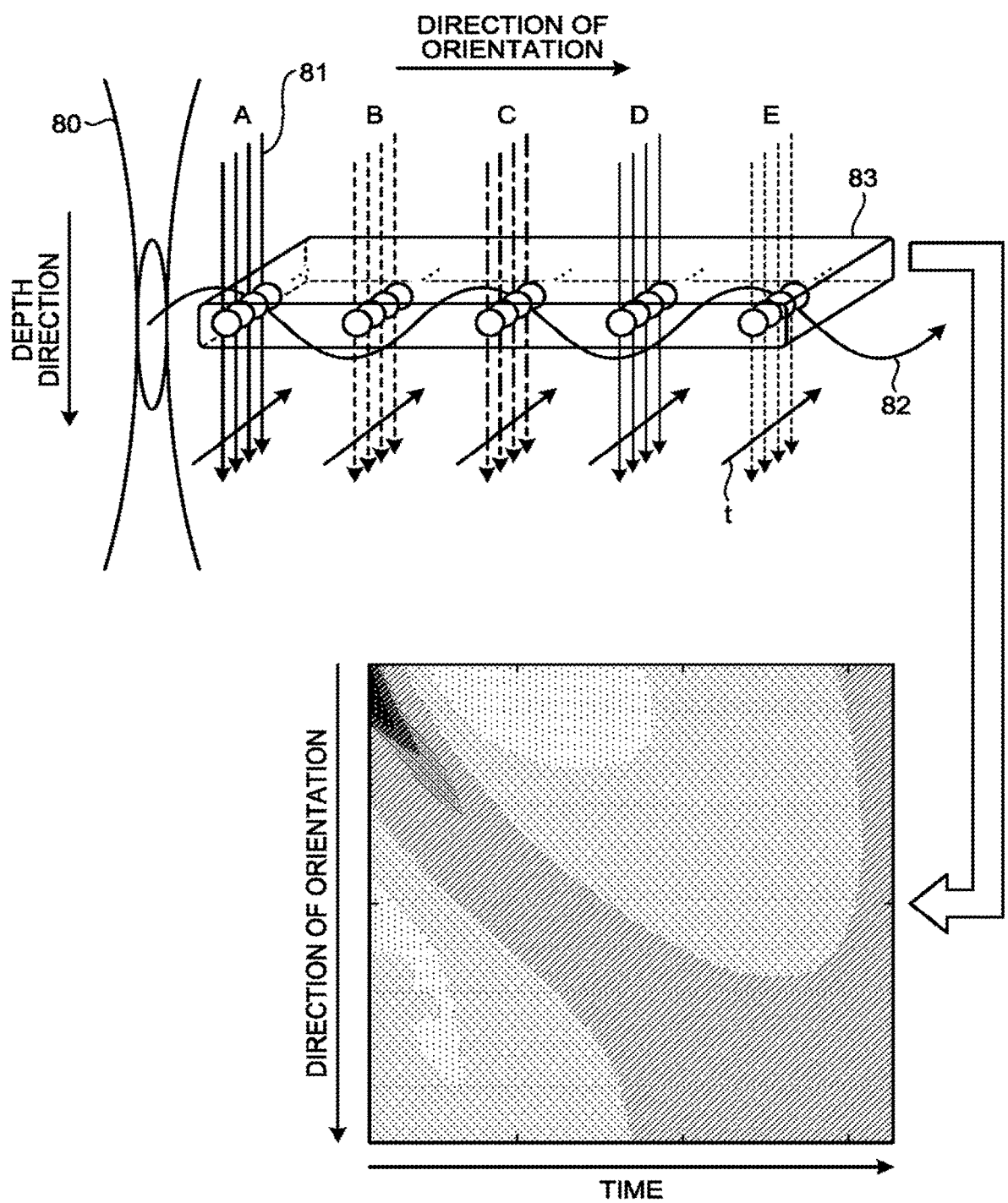
FIG. 17 is a drawing illustrating a relationship between viscosity index values and sampling positions according to yet another embodiment.

FIG. 17 is a drawing illustrating a relationship between viscosity index values and sampling positions according to yet another embodiment. FIG. 17 schematically illustrates a push pulse 80 and a tracking pulse 81 transmitted from the ultrasound probe 101, as well as a shear wave 82 and 92. In FIG. 17, the arrow t corresponds to the time direction.

As illustrated in the upper section of FIG. 17, the displacement caused by the shear wave 82 is measured multiple times in the time direction at the sampling points (the small circles in FIG. 17) on each of the scanning lines A, B, C, D, and E. Consequently, as illustrated in FIG. 17, a group of data 83 indicating temporal changes in the displacement at the sampling points on the scanning lines A, B, C, D, and E is measured. As illustrated in the bottom section of FIG. 17, the group of data 83 corresponds to a displacement distribution in the time-space directions on which the two-dimensional Fourier transform is performed.

In the example illustrated in FIG. 17, the signal processing function 131 assigns the index value indicating the viscosity calculated by performing the two-dimensional Fourier transform on a displacement distribution of the group of data 83 to the sampling points on the scanning line C positioned at the center among the scanning lines A to E. Further, the signal processing function 131 expresses the data into an image, by calculating the index value of viscosity at each of the sampling points in the depth direction and the direction of orientation (see FIG. 18).

Figure 18:
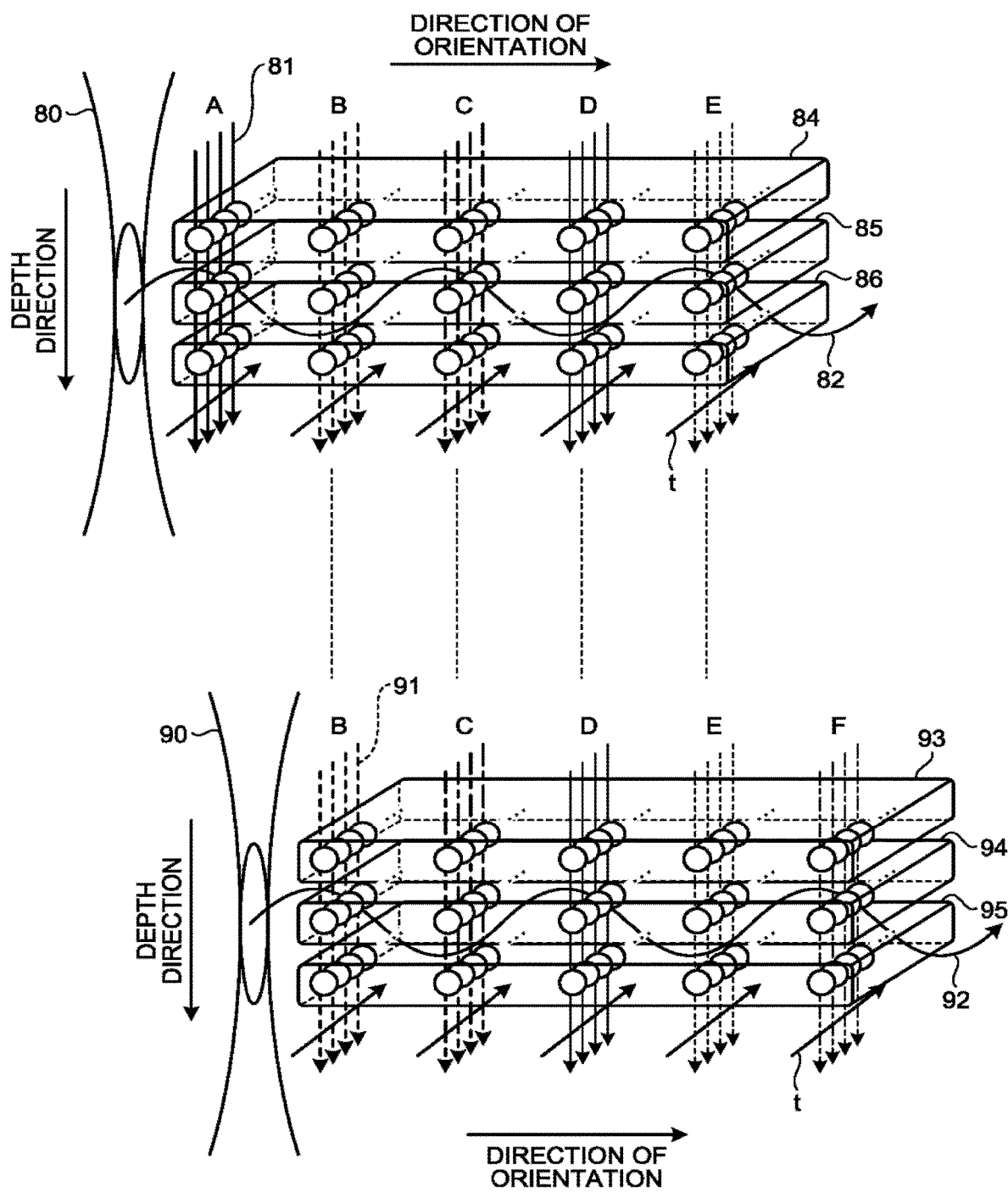
FIG. 18 is a drawing for explaining a process of calculating index values in a depth direction and a direction of orientation according to yet another embodiment.

FIG. 18 is a drawing for explaining the process of calculating the index values in the depth direction and the direction of orientation according to said yet another embodiment. FIG. 18 schematically illustrates push pulses 80 and 90 and tracking pulses 81 and 91 transmitted from the ultrasound probe 101, as well as shear waves 82 and 91. In FIG. 18, the arrow t corresponds to the time direction.

As illustrated in the top section of FIG. 18, the signal processing function 131 is configured to calculate an index value indicating viscosity for each of a groups of data 84, 85, and 86 having mutually-different depth directions. More specifically, by performing a two-dimensional Fourier transform on a displacement distribution of the group of data 84, the signal processing function 131 calculates an index value at the sampling points on the scanning line C included in the group of data 84. Further, by performing a two-dimensional Fourier transform on a displacement distribution of the group of data 85, the signal processing function 131 calculates an index value at the sampling points on the scanning line C included in the group of data 85. Furthermore, by performing a two-dimensional Fourier transform on a displacement distribution of the group of data 86, the signal processing function 131 calculates an index value at the sampling points on the scanning line C included in the group of data 86. In this manner, the signal processing function 131 calculates the index values at the sampling points in the depth direction.

As illustrated in the bottom section of FIG. 18, with regard to sampling points having mutually-different directions of orientation, the signal processing function 131 calculates the index values at the sampling points having the mutually-different directions of orientation, by moving the positions of the measured groups of data in the direction of orientation. More specifically, under the control of the processing circuitry 130, the transmission circuitry 110 moves the position of the group of data 84 into the position of a group of data 93. The group of data 93 includes the sampling points on the scanning lines B, C, D, E, and F. Further, the signal processing function 131 assigns the index values of viscosity calculated by performing a two-dimensional Fourier transform on a displacement distribution of the group of data 93, to the sampling points on the scanning line D positioned at the center among the scanning lines B to F. Furthermore, the transmission circuitry 110 moves the position of the group of data 85 into the position of a group of data 94. After that, the signal processing function 131 assigns the index values of viscosity calculated by performing a two-dimensional Fourier transform on a displacement distribution of the group of data 94 to the sampling points on the scanning line D positioned at the center among the scanning lines B to F. Further, the transmission circuitry 110 moves the position of the group of data 86 into the position of a group of data 95. After that, the signal processing function 131 assigns the index values of viscosity calculated by performing a two-dimensional Fourier transform on a displacement distribution of the group of data 95, to the sampling points on the scanning line D positioned at the center among the scanning lines B to F. In this manner, the signal processing function 131 calculates the index values at the sampling points in the direction of the orientation.

As explained above, the signal processing function 131 calculates the index values of the viscosity at the sampling points in the depth direction and the direction of orientation. Further, for example, the image processing function 132 generates an index image illustrated in FIG. 6, by assigning colors corresponding to the index values of the viscosity at the sampling points in the depth direction and the direction of orientation.

As explained above, the ultrasound diagnosis apparatus according to said yet another embodiment is able to calculate the index values indicating the viscosity, by performing the two-dimensional Fourier transform on the displacement distribution in the time-space directions. In other words, in the ultrasound diagnosis apparatus, the processing circuit is configured to detect the shear wave propagating in the object. Further, the processing circuit is configured to calculate the index value that indicates the viscosity within the object and that is not dependent on any physical model related to viscoelasticity, by analyzing the detected shear wave.

Other Index Values

Figure 19A:
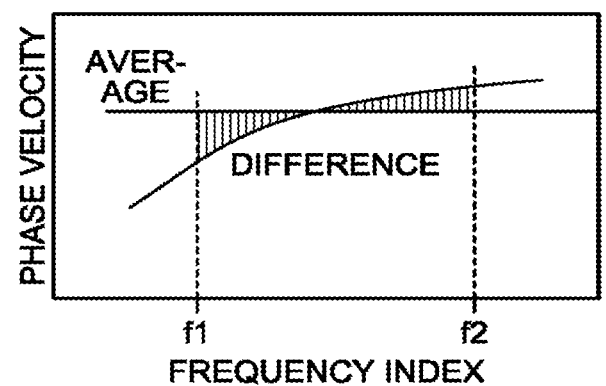
FIGS. 19A and 19B are drawings illustrating examples of other index values according to yet another embodiment.
Figure 19B:
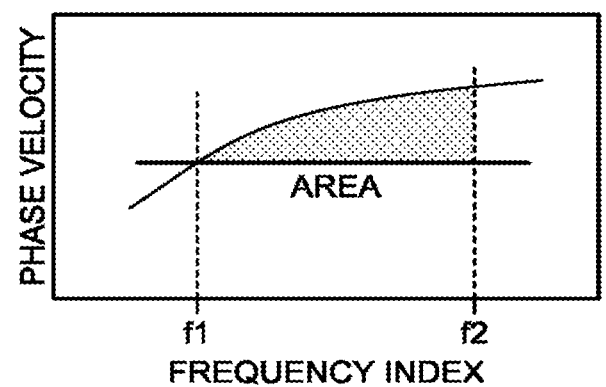

Further, for example, in the embodiments above, the example is explained in which the slope of the phase velocity distribution is calculated as the index value indicating the variance of the phase velocity values; however, possible embodiments are not limited to this example. For instance, the signal processing function 131 may calculate, as an index value indicating the variance of the phase velocity values, a sum of squares of differences from an average of phase velocity values in a certain frequency section (see FIG. 19A) or an area of phase velocity values in a certain frequency section (see FIG. 19B). In other words, the index value includes at least one selected from among the following calculated by analyzing the shear wave: a slope calculated by using one selected from between a frequency/phase velocity distribution and a frequency/phase difference distribution; a residual sum of squares; and an area. FIGS. 19A and 19B are drawings illustrating examples of the other index values according to yet another embodiment.

Further, for example, in the embodiments above, the example is explained in which the shear wave 12 generated by the push pulse is detected; however, possible embodiments are not limited to this example. For instance, the processing circuitry 130 may detect a shear wave generated by vibration applied from outside.

Further, for example, in the embodiments above, the example is explained in which the shear wave is detected by using the signal acquired by using the reflection of the ultrasound wave; however, possible embodiments are not limited to this example. For instance, the processing circuitry 130 may detect the shear wave, by using a signal acquired by using magnetic resonance. For example, the processing circuitry 130 is applicable to Magnetic Resonance (MR) elastography configured to evaluate firmness of a human body by using a signal acquired by performing a Magnetic Resonance Imaging (MRI) process.

The constituent elements of the apparatuses illustrated in the drawings are based on functional concepts. Thus, it is not necessary to physically configure the constituent elements as indicated in the drawings. In other words, the specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed in the apparatuses may be realized by a CPU and a computer program analyzed an executed by the CPU or may be realized as hardware using wired logic.

With regard to the processes explained in the embodiments described above, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, the specific names, information including various types of data and parameters that are presented in the above text and the drawings.

Further, it is possible to realize the image processing method explained in the embodiments above by causing a computer such as a personal computer or a workstation to execute an image processing program prepared in advance. The image processing method may be distributed via a network such as the Internet. Further, the image processing method may be recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like so as to be executed as being read from the recording medium by a computer.

According to at least one aspect of the embodiments described above, it is possible to accurately evaluate the viscosity of the tissue in the human body.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analyzing apparatus comprising processing circuitry configured:
    to detect a shear wave propagating in an object; and
    to calculate an index value that indicates viscosity within the object and that is not dependent on any physical model related to viscoelasticity, the index value indicating a change of a phase difference or a change of a phase velocity value by using a frequency/phase velocity distribution or a frequency/phase difference distribution that was calculated by analyzing the detected shear wave.

2. The analyzing apparatus according to claim 1, wherein the index value includes at least one of the following calculated by analyzing the shear wave: a slope calculated by using the frequency/phase velocity distribution or the frequency/phase difference distribution; a residual sum of squares; and an area.

3. The analyzing apparatus according to claim 1, wherein the processing circuitry generates an index image by assigning an attribute corresponding to the index value to a position corresponding to a calculation position of a phase difference or a phase velocity value calculated by analyzing the shear wave.

4. The analyzing apparatus according to claim 3, wherein the processing circuitry calculates a statistic value that uses the index value included in a region of interest set in the index image.

5. The analyzing apparatus according to claim 4, wherein the processing circuitry outputs the statistic value to a report generating computer program.

6. The analyzing apparatus according to claim 3, wherein the processing circuitry generates at least one of: an image indicating a tissue characteristic within the object; or an image based on a propagation time period taken for the shear wave to propagate to each of the plurality of positions, and
    the processing circuit displays the image simultaneously with the index image.

7. The analyzing apparatus according to claim 6, wherein
    as the image based on the propagation time period, the processing circuitry generates at least one of: an image obtained by assigning a pixel value corresponding to the propagation time period; an image obtained by assigning a pixel value corresponding to an elasticity level of a tissue in a human body calculated from the propagation time period; an image indicating positions having a same propagation time period as each other; or an image obtained by assigning a pixel value corresponding to a variance value of the propagation time period, and the processing circuitry displays the generated image simultaneously with the index image.

8. The analyzing apparatus according to claim 7, wherein, when a first region of interest is set in one of the images simultaneously displayed, the processing circuitry sets a second region of interest in such a position in another of the images that corresponds to the first region of interest, and the processing circuitry calculates a statistic value that uses values included the regions of interest, with respect to each of the first and the second regions of interest that were set.

9. The analyzing apparatus according to claim 1, wherein the processing circuitry calculates a statistic value that uses two or more of the index values.

10. The analyzing apparatus according to claim 1, wherein, when detecting the shear wave in each of a plurality of mutually-different scan ranges, the processing circuitry arranges at least one position in adjacently-positioned scan ranges to be scanned in a duplicate manner and further joins together phases calculated in positions included in the adjacently-positioned scan ranges, by using a phase in a position scanned in the duplicate manner.

11. The analyzing apparatus according to claim 1, wherein the processing circuitry calculates a phase by performing a frequency analysis on the shear wave detected with respect to each of a plurality of positions arranged along a propagation direction of the shear wave, the phase corresponding to a specific frequency component included in the shear wave.

12. The analyzing apparatus according to claim 11, wherein, before performing the frequency analysis, the processing circuitry performs a window function processing process by correcting a difference in propagation time periods of the shear wave detected in the plurality of positions, with respect to the shear wave detected in each of the plurality of positions.

13. The analyzing apparatus according to claim 1, wherein the processing circuitry detects the shear wave, by calculating movements within the object in a plurality of positions arranged along a propagation direction of the shear wave.

14. The analyzing apparatus according to claim 13, wherein, as the movements within the object, the processing circuitry calculates displacements, velocity values, or acceleration values in the plurality of positions arranged along the propagation direction of the shear wave.

15. The analyzing apparatus according to claim 1, wherein the processing circuitry calculates the index value by using a phase difference or a phase velocity value calculated by analyzing the shear wave, with respect to each of three or more frequency components.

16. The analyzing apparatus according to claim 1, wherein the processing circuitry calculates a phase difference or a phase velocity value, by using a phase calculated by analyzing the shear wave with respect to each of three or more positions.

17. The analyzing apparatus according to claim 1, wherein the processing circuitry detects the shear wave by using a signal acquired by using a reflection of an ultrasound wave or magnetic resonance.

18. The analyzing apparatus according to claim 1, wherein the processing circuitry detects the shear wave generated by an acoustic radiation force or vibration applied from outside.

19. The analyzing apparatus according to claim 1, wherein the processing circuitry generates a chart by plotting, for each frequency component, a phase difference or a phase velocity value calculated by analyzing the shear wave.

20. An analyzing apparatus comprising processing circuitry configured:
  to detect a shear wave propagating in an object with respect to each of a plurality of positions arranged along a propagation direction of the shear wave;
  to calculate a phase corresponding to a specific frequency component included in the shear wave;
  to calculate a phase difference or a phase velocity value by using the phase calculated with respect to each of the plurality of positions; and
  to generate an index image by using a value indicating a change of the phase difference or a change of the phase velocity value by using a frequency/phase velocity distribution or a frequency/phase difference distribution that was calculated as an index value indicating viscosity within the object and further assigning an attribute corresponding to the index value to a position corresponding to a calculation position of the phase difference or the phase velocity value.

* * * * *